United States Patent
Harada et al.

(10) Patent No.: US 9,654,743 B2
(45) Date of Patent: May 16, 2017

(54) ELECTRONIC DEVICE, INFORMATION PROVIDING SYSTEM, CONTROL METHOD, AND CONTROL PROGRAM

(71) Applicant: KYOCERA Corporation, Kyoto-shi, Kyoto (JP)

(72) Inventors: Naoki Harada, Machida (JP); Tomoyasu Takahashi, Kawasaki (JP); Hiroki Itou, Yokohama (JP); Kazuaki Nakae, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 14/424,297

(22) PCT Filed: Aug. 27, 2013

(86) PCT No.: PCT/JP2013/072915
§ 371 (c)(1),
(2) Date: Feb. 26, 2015

(87) PCT Pub. No.: WO2014/034683
PCT Pub. Date: Mar. 6, 2014

(65) Prior Publication Data
US 2015/0229888 A1     Aug. 13, 2015

(30) Foreign Application Priority Data

| Aug. 29, 2012 | (JP) | 2012-188808 |
| Sep. 5, 2012 | (JP) | 2012-195484 |
| Sep. 7, 2012 | (JP) | 2012-197763 |

(51) Int. Cl.
*H04N 5/225* (2006.01)
*H04N 7/18* (2006.01)
(Continued)

(52) U.S. Cl.
CPC ........... *H04N 7/185* (2013.01); *A61B 5/0046* (2013.01); *A61B 5/6898* (2013.01); *A61B 5/743* (2013.01);
(Continued)

(58) Field of Classification Search
CPC ...................................................... H04N 7/185
(Continued)

(56) References Cited

U.S. PATENT DOCUMENTS

| 6,450,647 B1 * | 9/2002 | Takeuchi ......................... 353/69 |
| 6,909,793 B1 * | 6/2005 | Mori .................. A61B 5/02055 348/14.07 |

(Continued)

FOREIGN PATENT DOCUMENTS

| JP | 2001-224557 A | 8/2001 |
| JP | 2005-319216 A | 11/2005 |

(Continued)

OTHER PUBLICATIONS

International Search Report mailed Oct. 8, 2013 in corresponding International Application No. PCT/JP2013/072915.

(Continued)

*Primary Examiner* — Roberto Velez
*Assistant Examiner* — Stephen Coleman
(74) *Attorney, Agent, or Firm* — Hauptman Ham, LLP

(57) ABSTRACT

According to one of aspects, an electronic device includes: a camera; a controller configured to determine whether a measured value of a healthcare device is included in an image captured by the camera; and a communication unit configured to transmit information related to the measured value to an information providing device when the measured value is included in the image.

18 Claims, 29 Drawing Sheets

(51) Int. Cl.
*A61B 5/00* (2006.01)
*G06K 9/00* (2006.01)
*H04N 5/262* (2006.01)

(52) U.S. Cl.
CPC ....... *G06K 9/00664* (2013.01); *H04N 5/2628* (2013.01); *A61B 5/4869* (2013.01); *G06K 2209/03* (2013.01)

(58) Field of Classification Search
USPC ...................................................... 348/207.1
See application file for complete search history.

(56) References Cited

U.S. PATENT DOCUMENTS

| | | | |
|---|---|---|---|
| 2006/0017959 A1* | 1/2006 | Downer | G07D 7/20 358/1.14 |
| 2006/0045389 A1* | 3/2006 | Butterworth | G01D 4/004 382/321 |
| 2006/0071950 A1* | 4/2006 | Kurzweil et al. | 345/698 |
| 2007/0177864 A1* | 8/2007 | Takahashi | 396/287 |
| 2007/0213938 A1* | 9/2007 | Kai | 702/19 |
| 2008/0027295 A1 | 1/2008 | Nakagawa et al. | |
| 2010/0043004 A1* | 2/2010 | Tambi et al. | 718/103 |
| 2012/0098992 A1* | 4/2012 | Hosoe | 348/222.1 |
| 2012/0134588 A1* | 5/2012 | Zhang | G06K 9/3275 382/176 |

FOREIGN PATENT DOCUMENTS

| | | |
|---|---|---|
| JP | 2008-033834 A | 2/2008 |
| JP | 2008-067321 A | 3/2008 |
| JP | 2011-199479 A | 10/2011 |
| JP | 2012-183269 A | 9/2012 |
| WO | 2011/145335 A1 | 11/2011 |

OTHER PUBLICATIONS

Office Action mailed Sep. 1, 2015, corresponding to Japanese patent application No. 2012-197763, for which an explanation of relevance is attached.

Office Action mailed Apr. 7, 2015, corresponding to Japanese patent application No. 2012-100455, for which an explanation of relevance is attached.

* cited by examiner

FIG.8

| USER ID | TIMESTAMP | TYPE | MEASURED VALUE A | | MEASURED VALUE B | | ... | MEASURED VALUE N | |
|---|---|---|---|---|---|---|---|---|---|
| | | | NAME | VALUE | NAME | VALUE | | NAME | VALUE |
| U001 | 2012/4/22 8:37 | Body composition meter | Body weight | 52.2 kg | Body fat percentage | 22.80% | ... | - | - |
| U001 | 2012/4/22 23:53 | Activity meter | Steps | 5950 steps | Consumed calorie | 402 Kcal | ... | - | - |
| ... | ... | ... | ... | ... | ... | ... | ... | ... | ... |

↙ 306

FIG.15
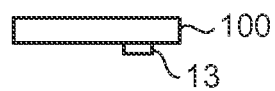

FIG.27
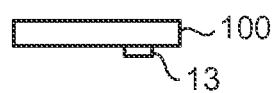
FIG.28
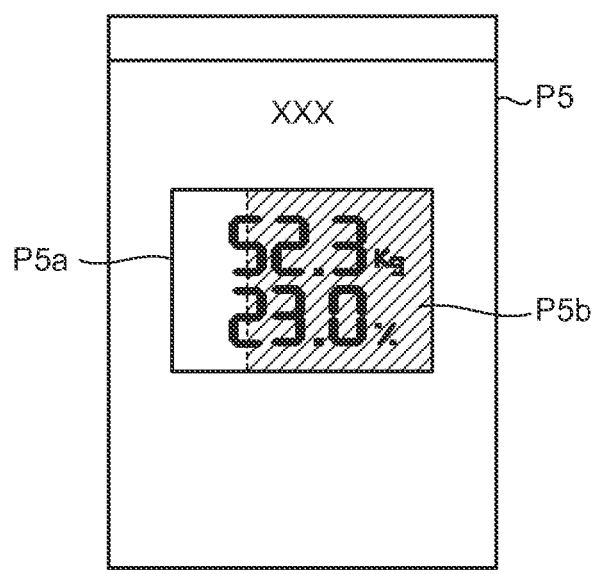

FIG.29
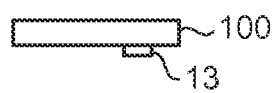
FIG.30
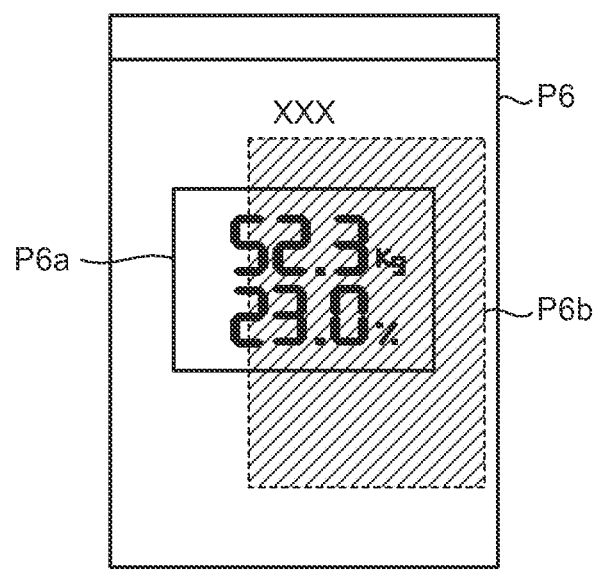

FIG.31
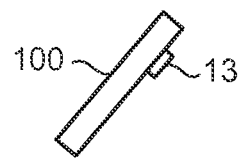
FIG.32
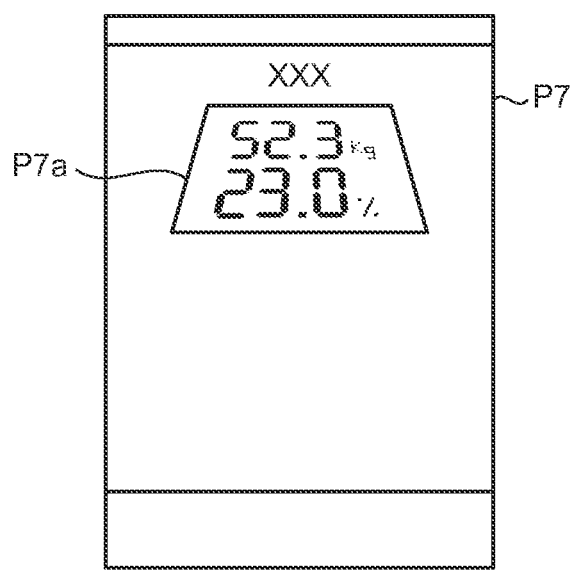

ELECTRONIC DEVICE, INFORMATION PROVIDING SYSTEM, CONTROL METHOD, AND CONTROL PROGRAM

CROSS-REFERENCE TO RELATED APPLICATION

This application is a National Stage of PCT international application Ser. No. PCT/JP2013/072915 filed on Aug. 27, 2013 which designates the United States, incorporated herein by reference, and which is based upon and claims the benefit of priority from Japanese Patent Applications No. 2012-188808 filed on Aug. 29, 2012, No. 2012-195484 filed on Sep. 5, 2012, and No. 2012-197763 filed on Sep. 7, 2012, the entire contents of which are incorporated herein by reference.

FIELD

The present application relates to an electronic device, an information providing system, a control method, and a control program.

BACKGROUND

Various measuring instruments are used for healthcare, such as a bathroom scale for measuring body weight, a blood pressure monitor for measuring blood pressure, and a pedometer for counting steps. Some of the measuring instruments include those that have a communication function to transmit a measured value to an information processing device (see, for example, Patent Literature 1 and Patent Literature 2). The value transmitted to the information processing device is used for various analyses.

CITATION LIST

Patent Literature

Patent Literature 1: JP-A-2008-033834
Patent Literature 2: JP-A-2005-319216

Technical Problem

When individual measuring instruments are provided with the communication function, the configuration thereof is complicated, which leads to an increase in costs, and makes downsizing difficult. For the foregoing reasons, there is a need for an electronic device, an information providing system, a control method, and a control program capable of transmitting the value measured by a measuring instrument to another device without complicating the configuration of the measuring instrument.

SUMMARY

According to one of aspects, an electronic device includes: a camera; a controller configured to determine whether a measured value of a healthcare device is included in an image captured by the camera; and a communication unit configured to transmit information related to the measured value to an information providing device when the measured value is included in the image.

According to one of aspects, an information providing system includes an electronic device and an information providing device. The electronic device includes: a camera; a first controller configured to determine whether a measured value of a healthcare device is included in an image captured by the camera; and a communication unit configured to transmit information related to the measured value to the information providing device when the measured value is included in the image. The information providing device includes: a storage configured to store the information related to the measured value; and a second controller configured to perform analysis based on the information related to the measured value.

According to one of aspects, a control method is of an electronic device with a camera. The control method includes: determining whether a measured value of a healthcare device is included in an image captured by the camera; storing information related to the measured value in a storage; and performing analysis for providing information based on the stored information related to the measured value.

According to one of aspects, a control program causes an electronic device with a camera to execute: determining whether a measured value of a healthcare device is included in an image captured by the camera; storing information related to the measured value in a storage; and performing analysis for providing information based on the stored information related to the measured value.

BRIEF DESCRIPTION OF DRAWINGS

FIG. 8 is a diagram of one of examples of measured value information.
FIG. 15 is a diagram of one of examples of when an indicator of the body composition meter is captured under a light source.

FIG. 27 is a diagram of one of examples of how the mobile phone itself unexpectedly appears in an image.

FIG. 28 is a diagram of one of examples of an image in which the mobile phone itself unexpectedly appears.

FIG. 29 is a diagram of one of examples of how a shadow of the mobile phone unexpectedly appears in an image.

FIG. 30 is a diagram of one of examples of an image in which a shadow of the mobile phone unexpectedly appears.

FIG. 31 is a diagram of one of examples of a state in which the unexpected appearance does not occur.

FIG. 32 is a diagram of one of examples of an image captured in the state illustrated in FIG. 31.

DESCRIPTION OF EMBODIMENTS

Exemplary embodiments for implementing the present invention will be explained in detail below with reference to the accompanying drawings. In the following embodiments, a mobile phone will be explained as one of examples of the electronic device.

Embodiment 1

Figure 1:
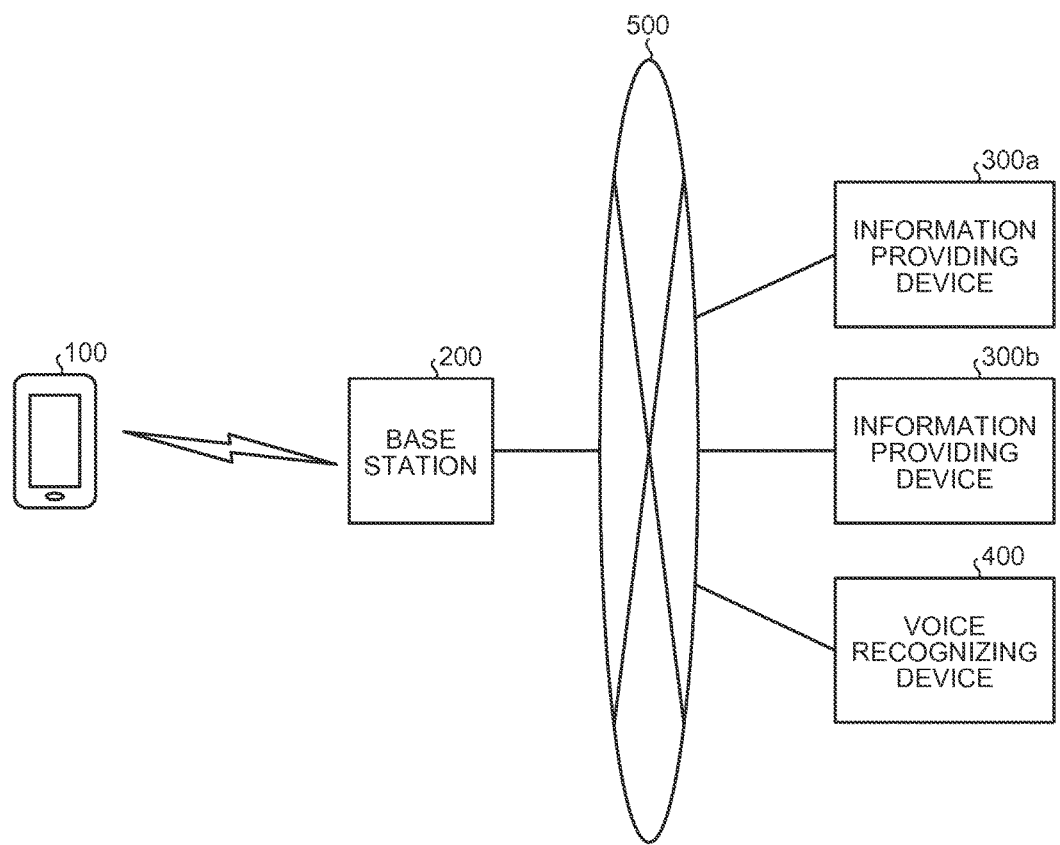
FIG. 1 is a diagram of a configuration of an information providing system according to one of embodiments.

A configuration of an information providing system according to one of embodiments will be explained with reference to FIG. 1. FIG. 1 is a diagram of the configuration of the information providing system according to the embodiment. As illustrated in FIG. 1, the information providing system includes a mobile phone 100, a base station 200, information providing devices 300a and 300b, and a voice recognizing device 400. In the description below, the information providing devices 300a and 300b may be collectively referred to as an information providing device 300 without specifying which is which.

The mobile phone 100 has a function of reading a measured value measured by a healthcare device and transmitting the read value to the information providing device 300. The healthcare device is a measuring instrument for measuring numerical values related to health. Examples of the healthcare device include, but are not limited to, a bathroom scale for measuring body weight, a body composition meter for measuring body fat percentage and the like in addition to the body weight, a thermometer for measuring body temperature, a blood pressure monitor for measuring blood pressure, a pulse meter for measuring pulses, a pedometer for counting steps, and an activity meter for measuring an amount of activity due to exercise including walking.

The mobile phone 100 captures the healthcare device by a camera to read a measured value displayed in the indicator provided in the healthcare device. By capturing the measured value displayed in the indicator using the camera in this way, the mobile phone 100 can read the measured value measured by the healthcare device even if the healthcare device does not have a communication function. The read measured value is transmitted to the information providing device 300 through the communication function provided in the mobile phone 100. The details of how the mobile phone 100 reads the measured value will be explained later.

The base station 200, the information providing device 300, and the voice recognizing device 400 are communicably connected to each other through a network 500.

The base station 200 establishes a radio communication path with the mobile phone 100 located within a communication range, which allows the mobile phone 100 to communicate with other device via the radio communication path. Hereinafter, when the communication of the mobile phone 100 is to be explained, description of the base station 200 may be omitted for the sake of simplicity of description.

The information providing device 300 stores the measured value transmitted from the mobile phone 100, in association with an ID (identifier) of a user of the mobile phone 100 and a date and time (timestamp). The information providing device 300 can store measured values of a plurality of types of healthcare devices in association with respective identifiers of users. The information providing device 300 performs analysis processing based on the measured values accumulated in this way and transmits information such as advice about health to the mobile phone 100. There are a plurality of information providing devices 300, and each of them is operated by a different operator.

The voice recognizing device 400 analyzes the content of voice information transmitted from other device by performing voice recognition processing thereon, and transmits the analyzed content to a source device. For example, when the mobile phone 100 transmits voice information in which user's voice is recorded to the voice recognizing device 400, the voice recognizing device 400 analyzes the content of the voice information through the voice recognition processing and transmits the analyzed content as text data to the mobile phone 100. With this system, a voice operation of the mobile phone 100 is implemented.

The configuration of the information providing system is not limited to the example illustrated in FIG. 1. For example, the number of various devices included in the information providing system may be larger or smaller than the number illustrated in FIG. 1. The information providing system does not have to include the voice recognizing device 400. The information providing device 300 may be a personal computer in the home and the base station 200 may be a wireless LAN router in the home.

Figure 2:
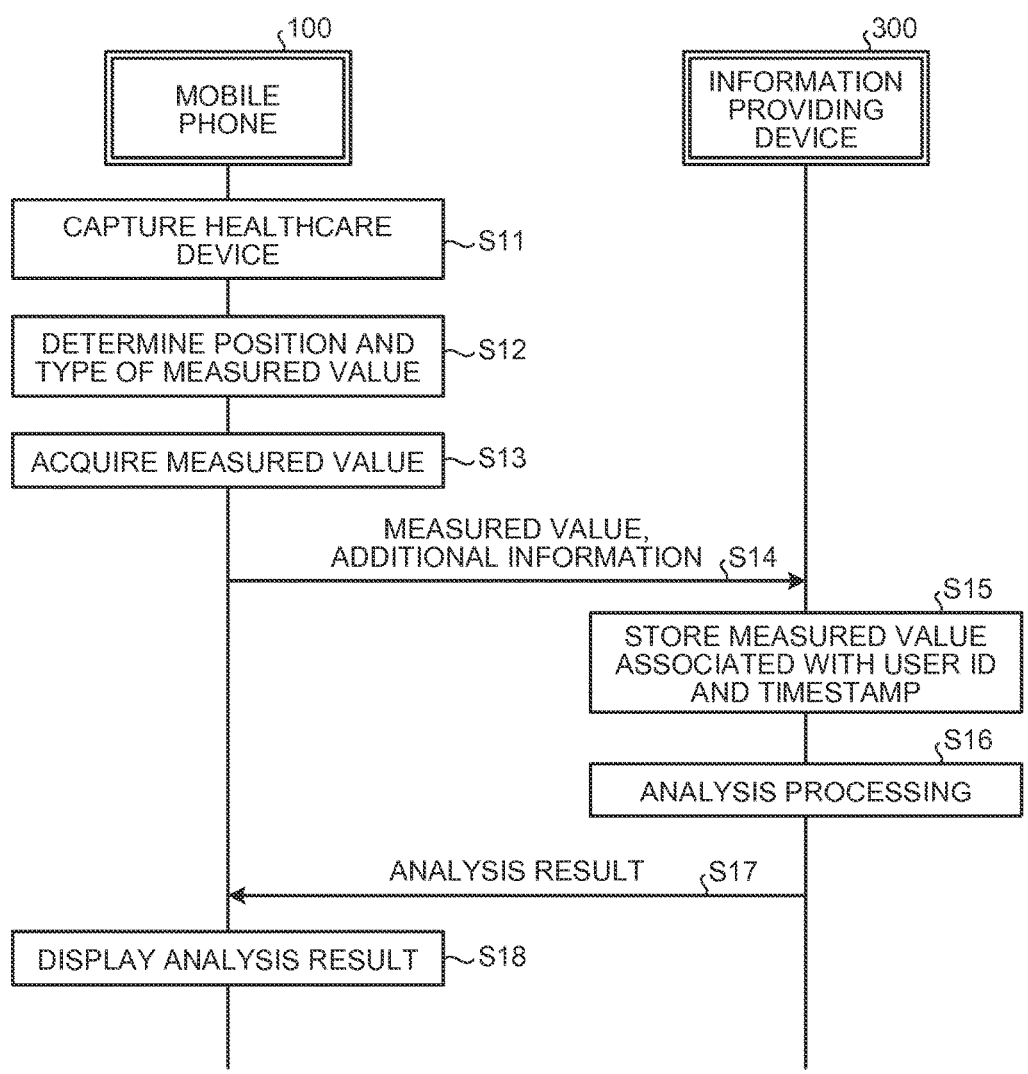
FIG. 2 is a diagram of an outline of an operation of the information providing system.

The outline of an operation of the information providing system will be explained with reference to FIG. 2. FIG. 2 is a diagram of the outline of the operation of the information providing system. It is assumed that a healthcare device performs measurement and measured values are displayed in the indicator of the healthcare device before the operation illustrated in FIG. 2. In this state, the mobile phone 100 captures an image of the healthcare device using a camera (Step S11). The mobile phone 100 then determines a position and a type of a measured value included in a captured image (Step S12). In the present application, capturing an image is not limited to acquiring an image when a shutter is released (when a release button is pressed), but includes, like so-called a live view, acquiring continuously videos (images) being captured while displaying them on the display.

After the determination of the position and the type of the measured value in this way, the mobile phone 100 reads the measured value from the captured image (Step S13). Reading the measured value included in the image can be implemented by using known character recognition technology. The mobile phone 100 transmits the read measured value along with additional information to the information providing device 300 (Step S14). The additional information is necessary information for using the measured value in the information providing device 300 for analysis. Examples of the additional information include, but are not limited to, a value indicating a type of the measured value, a value indicating a unit of the measured value, etc.

When a plurality of measured values are read from the captured image, the mobile phone 100 may separately transmit the measured values or may collectively transmit the measured values. The mobile phone 100 may store the measured values acquired from a plurality of types of healthcare devices and collectively transmit the acquired measured values to the information providing device 300 at a certain timing. In this case, the mobile phone 100 stores dates and times on which the measured values are acquired in association with the respective measured values and includes the stored dates and times in the additional information at the time of transmission.

When there are a plurality of information providing devices 300, the mobile phone 100 may transmit the measured values and the additional information to a preset information providing device 300, or may determine an information providing device 300 as a destination according to information such as a maker and a type acquired from the captured image.

The information providing device 300 stores the measured values transmitted from the mobile phone 100 in association with an ID of a user of the mobile phone 100 and the timestamp (Step S15). The ID of the user may be acquired from the additional information or may be acquired based on a header value of a packet for transmitting the measured values from the mobile phone 100 to the information providing device 300. The timestamp may be acquired from the additional information, or may be acquired based on a value of a timer unit of the information providing device 300 of when the measured value is received. When acquired from the additional information, the timestamp indicates a date and time on which the measured value is read or a date and time on which the measured value is transmitted, and when acquired based on the value of the timer unit of the information providing device 300, the timestamp indicates a date and time on which the measured value is received.

Thereafter, the information providing device 300 performs analysis processing based on the stored measured value (Step S16). The analysis processing may be performed each time when any measured value is received, or may be performed each time when a specific type of measured value (for example, body weight) is received. Alternatively, the analysis processing may be performed at a preset time.

In the analysis processing, analysis about health is performed based on chronological changes or the like of the measured values related to the user of the mobile phone 100. Because measured values related to a plurality of users are accumulated in the information providing device 300, the information providing device 300 may use the information obtained by statistically processing the measured values related to the users, in the analysis processing.

The information providing device 300 transmits an analysis result to the mobile phone 100 (Step S17). The mobile phone 100 displays the received analysis result (Step S18). The analysis result may be transmitted to the mobile phone 100 as electronic mail or may be transmitted to the mobile phone 100 in any other predetermined format. It may be configured such that the measured value and the additional information are transmitted as HTTP (HyperText Transfer Protocol) request and the analysis result is responded in HTML (HyperText Markup Language) format.

In this way, by accumulating the measured values read from the healthcare device and analyzing them, the information difficult for the user to notice from individual measured values can be provided to the user.

Figure 3:
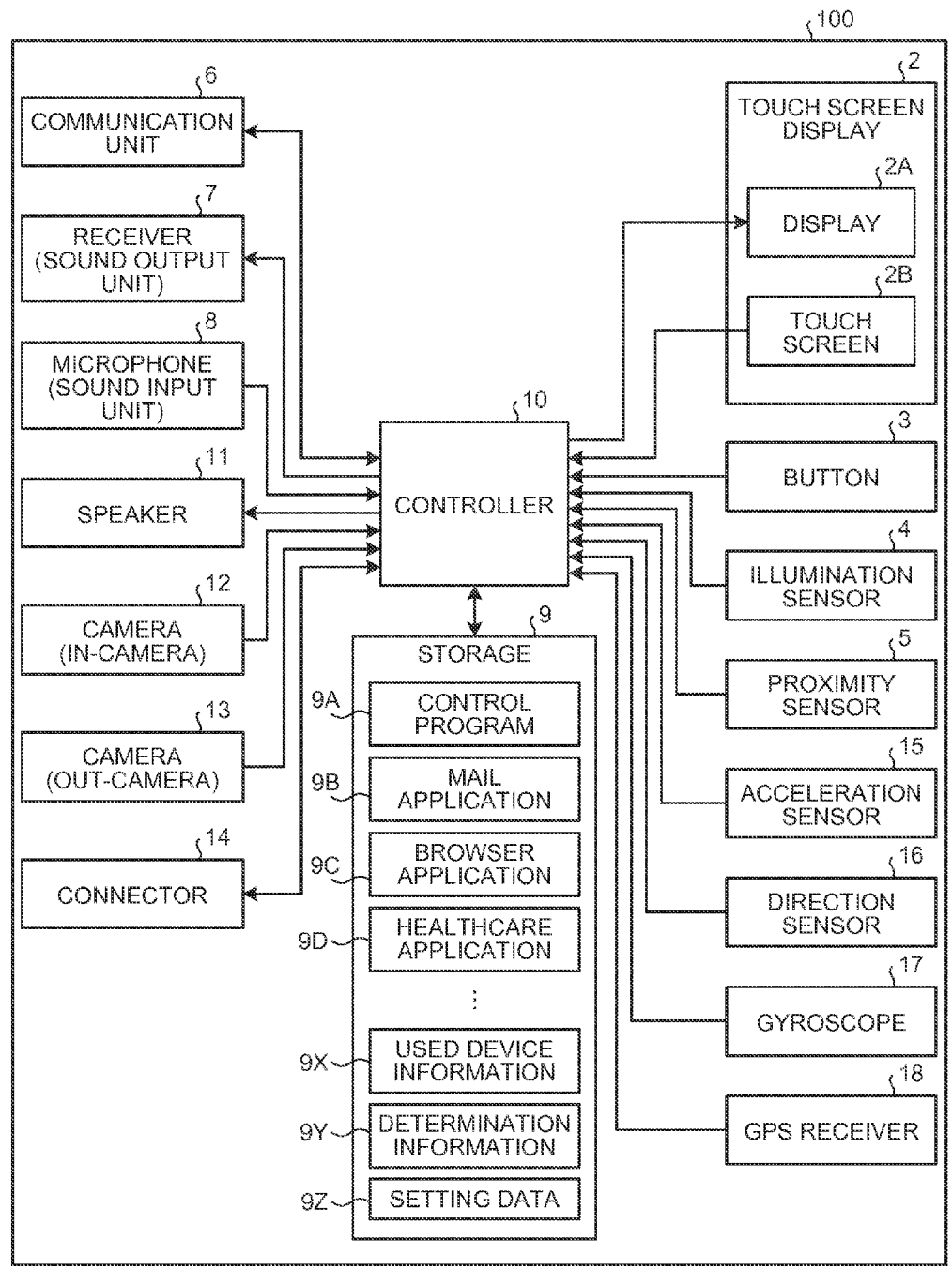
FIG. 3 is a block diagram of a mobile phone.

The configuration of the mobile phone 100 will be explained with reference to FIG. 3. FIG. 3 is a block diagram of the mobile phone 100. As illustrated in FIG. 3, the mobile phone 100 includes a touch screen display 2, a button 3, an illumination sensor 4, a proximity sensor 5, a communication unit 6, a receiver 7, a microphone 8, a storage 9, a controller 10, a speaker 11, a camera 12, a camera 13, a connector 14, an acceleration sensor 15, a direction sensor 16, a gyroscope 17, and a GPS (Global Positioning System) receiver 18.

The touch screen display 2 includes a display 2A and a touch screen 2B. The display 2A is provided with a display device such as an LCD (Liquid Crystal Display), an OELD (Organic Electro-Luminescence Display), or an IELD (Inorganic Electro-Luminescence Display). The display 2A displays text, images, symbols, graphics, and the like.

The touch screen 2B detects a contact of a finger, a pen, a stylus pen, or the like on the touch screen 2B. The touch screen 2B can detect positions where a plurality of fingers, pens, stylus pens, or the like make contact with the touch screen 2B. In the following explanation, a finger, a pen, a stylus pen, or the like which comes in contact with the touch screen 2B may be called "contact object"

The detection method of the touch screen 2B may be any detection method such as a capacitive type detection method, a resistive type detection method, a surface acoustic wave type (or ultrasonic type) detection method, an infrared type detection method, an electro magnetic induction type detection method, and a load sensing type detection method.

In the description herein below, for the sake of simplicity, it is assumed that the user uses his/her finger(s) to make contact with the touch screen 2B in order to operate the mobile phone 100.

The mobile phone 100 determines a type of a gesture based on at least one of a contact detected by the touch screen 2B, a position where the contact is detected, a change of the position where the contact is detected, an interval between detected contacts, and the number of detection times of the contact. The gesture is an operation performed on the touch screen 2B. Examples of the gestures determined by the mobile phone 100 include, but are not limited to, touch, long touch, release, swipe, tap, double tap, long tap, drag, flick, pinch in, and pinch out. In the description herein below, for the sake of simplicity, a case of "the touch screen detects a contact and the mobile phone 100 determines that the type of the gesture is X based on the contact" may be described as "the mobile phone 100 detects X", "the controller detects X", or "the touch screen detects X". The controller will be explained later.

The button 3 is operated by the user. The controller 10 detects an operation for the button 3 in cooperation with the button 3. Examples of the operations for the button 3 include, but are not limited to, a click, a double click, a triple click, a push, and a multi-push.

The illumination sensor 4 detects illumination of the ambient light of the mobile phone 100. The illumination indicates intensity of light, lightness, or brightness. The illumination sensor 4 is used, for example, to adjust the brightness of the display 2A. The proximity sensor 5 detects the presence of a nearby object without any physical contact. The proximity sensor 5 detects the presence of the object based on a change of the magnetic field or a change of the return time of the reflected ultrasonic wave, etc. The proximity sensor 5 detects that, for example, the touch screen display 2 is brought close to someone's face. The illumination sensor 4 and the proximity sensor 5 may be configured as one sensor. The illumination sensor 4 can be used as a proximity sensor.

The communication unit 6 performs communication via radio waves. A communication system supported by the communication unit 6 is wireless communication standard. The wireless communication standard includes, for example, a communication standard of cellular phones such as 2G, 3G, and 4G. The communication standard of cellular phones includes, for example, LTE (Long Term Evolution), W-CDMA (Wideband Code Division Multiple Access), CDMA 2000, PDC (Personal Digital Cellular), GSM (registered trademark) (Global System for Mobile Communications), and PHS (Personal Handy-phone System). The wireless communication standard further includes, for example, WiMAX (Worldwide Interoperability for Microwave Access), IEEE 802.11, Bluetooth (registered trademark), IrDA (Infrared Data Association), and NFC (Near Field Communication). The communication unit 6 may support one or more communication standards.

The receiver 7 and the speaker 11 are sound output units. The receiver 7 and the speaker 11 output a sound signal transmitted from the controller 10 as sound. The receiver 7 is used, for example, to output voice of the other party on the phone call. The speaker 11 is used, for example, to output a ring tone and music. One of the receiver 7 and the speaker 11 may double as the other function. The microphone 8 is a sound input unit. The microphone 8 converts voice of the user or the like to a sound signal and transmits the converted signal to the controller 10.

The storage 9 stores therein programs and data. The storage 9 is used also as a work area that temporarily stores a processing result of the controller 10. The storage 9 may include any non-transitory storage medium such as a semiconductor storage medium and a magnetic storage medium. The storage 9 may include a plurality of types of storage mediums. The storage 9 may include a combination of a portable storage medium such as a memory card, an optical disc, or a magneto-optical disc with a reader of the storage medium. The storage 9 may include a storage device used as a temporary storage area such as Random Access Memory (RAM).

Programs stored in the storage 9 include applications executed in the foreground or the background and a control program for assisting operations of the applications. The application causes the controller 10, for example, to display a screen on the display 2A and perform processing according to a gesture detected through the touch screen 2B. The control program is, for example, an OS. The applications and the control program may be installed in the storage 9 through wireless communication by the communication unit 6 or through a non-transitory storage medium.

The storage 9 stores, for example, a control program 9A, a mail application 9B, a browser application 9C, a healthcare application 9D, used device information 9X, determination information 9Y, and setting data 9Z. The control program 9A provides functions related to various controls for operating the mobile phone 100. The control program 9A activates or terminates an application according to a detected operation, for example.

The mail application 9B provides an e-mail function for composition, transmission, reception, and display of e-mail, and the like. The browser application 9C provides a WEB browsing function for display of WEB pages.

The healthcare application 9D provides a function of reading a measured value displayed in an indicator of a healthcare device and transmitting the read value to the information providing device 300, and a function of displaying an analysis result transmitted from the information providing device 300 on the display 2A.

The used device information 9X includes information indicating features on the appearance of a healthcare device used by the user of the mobile phone 100 (hereinafter, it may be called "used device") and information indicating a position and a type of the measured value displayed by the healthcare device. The information indicating the features on the appearance of the healthcare device includes at least one of, for example, a shape (shape of the whole or part of the healthcare device), a color, a typeface of a measured value, a layout of the measured value, a character string or a symbol near the measured value, and other character or symbol on the surface of the healthcare device and its position. When a plurality of measured values are simultaneously displayed in the indicator of the healthcare device, information indicating the position and the type of the measured value includes information corresponding to each measured value. When the measured values displayed in the indicator of the healthcare device are changed, information indicating the position and the type of the measured value includes information related to the order of displaying the measured values.

As explained later, information is added to the used device information 9X each time the mobile phone 100 reads a measured value from a new healthcare device. The used device information 9X may initially have no information, or may store information corresponding to previously selected healthcare devices.

The determination information 9Y includes information for determining which measured value is present in which part of a captured image. Specifically, the determination information 9Y stores the information related to the features on the appearance and the information indicating the position and the type of a measured value displayed by a healthcare device in association with each other, for each healthcare device existing on the market. The information indicating the features on the appearance of a healthcare device includes at least one of, for example, a shape (shape of the whole or part of the healthcare device), a color, a typeface of a measured value, a layout of a measured value, a character string or a symbol near the measured value, and other character or symbol on the surface of the healthcare device and its position. When a plurality of measured values are simultaneously displayed in the indicator of the healthcare device, information indicating the position and the type of the measured value includes information corresponding to each measured value. When the measured values displayed in the indicator of the healthcare device are changed, information indicating the position and the type of the measured value includes information related to the order of displaying the measured values.

The determination information 9Y may combine a plurality of models whose features on the appearance are substantially the same as each other and in which the position and the type of the displayed measured value is the same as each other, to store the information as one healthcare device. The determination information 9Y does not have to cover the information related to all the healthcare devices existing on the market.

The determination information 9Y also includes abstracted information so as to read a measured value even from an unknown healthcare device. Specifically, the determination information 9Y stores information related to a character or a symbol likely to be present near the measured value, for each type of the measured value. In general, at least one of a name and a unit of a measured value is present near the measured value. By storing such a name or a unit associated with the type of the measured value, it becomes possible to detect a measured value near the name or the unit by using it as a clue and determine the type of the measured value. In this case, to facilitate detection of a measured value, a relative position of the measured value corresponding to the name or the unit may be stored along with the name and the unit. For example, when a unit is stored, description indicating the presence of a measured value on the left side of the unit may further be stored.

The determination information 9Y further stores information, as abstracted information, related to a range of measured values for each type of measured value. For example, when the measured value is a body temperature, a range from 35° C. to 40° C. is stored as its range. For example, when the measured value is systolic blood pressure, a range from 100 mmHg to 200 mmHg is stored as its range. When a numerical value is detected in the image, by checking the numerical value against the ranges, it is possible to determine whether the numerical value is a measured value and which type of measured value it is.

The determination information 9Y further stores information, as abstracted information, related to a layout of measured values. When a plurality of measured values are simultaneously displayed, the layout of measured values may have a regularity in each maker or each type of healthcare device. For example, when it is a pulse meter, systolic blood pressure, diastolic blood pressure, the number of pulses are, in many cases, vertically displayed in the order from the top. When a plurality of numerical values are detected in the image, by checking the layout of the numerical values against the regularity, it is possible to determine whether the numerical values are measured values and which type of the measured value each of them is.

The determination information 9Y also stores information used to determine a maker and a type of a healthcare device. Specifically, the determination information 9Y stores information related to a typeface of a displayed measured value for each maker. Furthermore, the determination information 9Y stores information related to a name or a symbol of a company to be printed on, to be stamped on, or to be attached to the surface of the healthcare device for each maker. Moreover, the determination information 9Y stores information related to a model number to be printed on, to be stamped on, or to be attached to the surface of the healthcare device for each maker and for each type of the healthcare device. The determination information 9Y stores information used to determine a maker and a type of the healthcare device associated with the information related to the features on the appearance of the healthcare device. The abstracted information included in the determination information 9Y may be stored for each maker or each type of the healthcare device.

The setting data 9Z includes information related to various settings for the operation of the mobile phone. 100.

The controller 10 is a processing unit. Examples of the processing unit include, but are not limited to, a CPU (Central Processing Unit), an SoC (System-on-a-chip), an MCU (Micro Control Unit), and an FPGA (Field-Programmable Gate Array). The controller 10 integrally controls the operations of the mobile phone 100 to implement the various functions.

Specifically, the controller 10 executes instructions included in the program stored in the storage 9 while referring to the data stored in the storage 9 as necessary. The controller 10 controls a function unit according to the data and the instructions to thereby implement the various functions. Examples of the function unit include, but are not limited to, the display 2A, the communication unit 6, the receiver 7, and the speaker 11. The controller 10 can change the control according to the detection result of a detector. Examples of the detector include, but are not limited to, the touch screen 2B, the button 3, the illumination sensor 4, the proximity sensor 5, the microphone 8, the camera 12, the camera 13, the acceleration sensor 15, the direction sensor 16, the gyroscope 17, and the GPS receiver 18.

The controller 10 executes, for example, the healthcare application 9D to thereby implement a function of reading a measured value displayed in an indicator of a healthcare device and transmitting the read measured value to the information providing device 300 and a function of displaying an analysis result transmitted from the information providing device 300 on the display 2A.

The camera 12 is an in-camera for capturing an object facing the front face. The camera 13 is an out-camera for capturing an object facing the back face. The camera 13 is also used to capture the healthcare device.

The connector 14 is a terminal to which another device is connected. The connector 14 may be a general-purpose terminal such as a USB (Universal Serial Bus), a HDMI (registered trademark) (High-Definition Multimedia Interface), Light Peak (Thunderbolt (registered trademark)), and an earphone/microphone connector. The connector 14 may be a dedicated terminal such as a Dock connector. Examples of the device connected to the connector 14 include, but are not limited to, an external storage, a speaker, and a communication device.

The acceleration sensor 15 detects a direction and a magnitude of acceleration applied to the mobile phone 100. The direction sensor 16 detects a direction of geomagnetism. The gyroscope 17 detects an angle and an angular velocity of the mobile phone 100. The detection results of the acceleration sensor 15, the direction sensor 16, and the gyroscope 17 are used in combination with each other in order to detect a position of the mobile phone 100 and a change of its attitude. The GPS receiver 18 detects a position of the mobile phone 100.

Part or all of the programs and the data stored in the storage 9 in FIG. 3 may be downloaded from any other device through wireless communication by the communication unit 6. Part or all of the programs and the data stored in the storage 9 in FIG. 3 may be stored in a non-transitory storage medium that can be read by a reader included in the storage 9. Part or all of the programs and the data stored in the storage 9 in FIG. 3 may be stored in a non-transitory storage medium that can be read by a reader connected to the connector 14. Examples of the non-transitory storage mediums include, but are not limited to, an optical disc such as CD (registered trademark), DVD (registered trademark), and Blu-ray (registered trademark), a magneto-optical disc, a magnetic storage medium, a memory card, and a solid-state storage medium.

The configuration of the mobile phone 100 illustrated in FIG. 3 is exemplarily illustrated, and therefore it can be modified as required within a scope that does not depart from the gist of the present invention. For example, in the example illustrated in FIG. 3, the mobile phone 100 is provided with two cameras; however, the mobile phone 100 may be provided with only the camera 13. In the example of FIG. 3, the mobile phone 100 is provided with four types of sensors in order to detect its position and attitude; however, the mobile phone 100 does not have to be provided with some of the sensors. Alternatively, the mobile phone 100 may be provided with any other type of sensor for detecting at least one of the position and the attitude.

Figure 4:
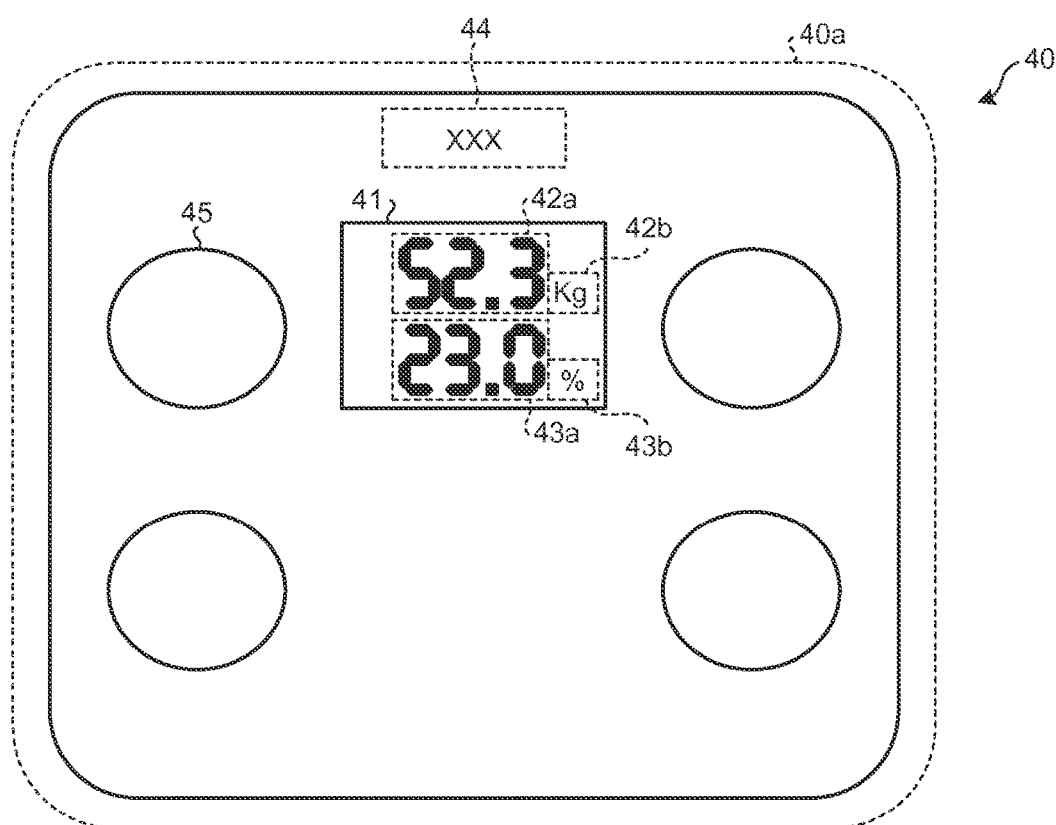
FIG. 4 is a diagram of one of examples of a body composition meter included in an image.

Examples of how the mobile phone 100 reads a measured value will be explained with reference to FIG. 4 to FIG. 6. FIG. 4 is a diagram of one of examples of a body composition meter 40 included in an image captured by the camera 13. The body composition meter 40 includes an indicator 41, a maker name 44 printed on the surface, and electrodes 45 for measuring body fat percentage. A measured value 42a indicating body weight and a measured value 43a indicating body fat percentage are displayed in the indicator 41. Furthermore, a unit 42b indicating that a unit of the body weight is Kg is displayed adjacently on the right side of the measured value 42a, and a symbol 43b indicating that the body fat percentage is expressed in percentage is displayed adjacently on the right side of the measured value 43a.

When the body composition meter 40 as described above is included in the image, the mobile phone 100 detects the measured value 42a and the measured value 43a which are numerical values, the unit 42b adjacent to the measured value 42a, and the symbol 43b adjacent to the measured value 43a. Moreover, the mobile phone 100 acquires information related to the features on the appearance of the body composition meter 40 including the measured value 42a and the measured value 43a. For example, a shape 40a of the body composition meter 40, a color of the body composition meter 40, a position of the indicator 41, a character style and layout of the information displayed in the indicator 41, characters forming the maker name 44, a character style and position of the maker name 44, positions of the electrode 45 and the electrode 45 are acquired as the information related to the features on the appearance.

The mobile phone 100 checks the acquired pieces of information against at least one of the used device information 9X and the determination information 9Y, to thereby determine that the measured value 42a indicates the body weight and the measured value 43a indicates the body fat percentage. The mobile phone 100 then acquires the body weight and the body fat percentage as numerical value data through the character recognition processing.

Figure 5:
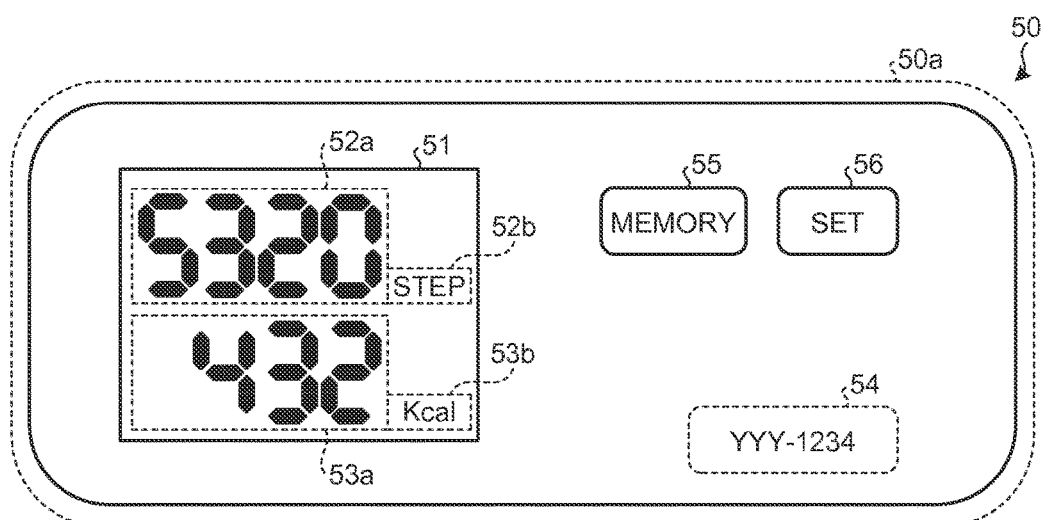
FIG. 5 is a diagram of one of examples of an activity meter included in an image.

FIG. 5 is a diagram of one of examples of an activity meter 50 included in an image captured by the camera 13. The activity meter 50 includes an indicator 51, a model number 54 printed on the surface, a button 55, and a button 56. A measured value 52a indicating steps and a measured value 53a indicating consumed calorie are displayed in the indicator 51. Furthermore, a unit 52b indicating that a unit of the steps is step (STEP) is displayed adjacently on the right side of the measured value 52a, and a unit 53b indicating that a unit of the consumed calorie is Kcal is displayed adjacently on the right side of the measured value 53a.

When the activity meter 50 as described above is included in the image, the mobile phone 100 detects the measured value 52a and the measured value 53a which are numerical values, the unit 52b adjacent to the measured value 52a, and the unit 53b adjacent to the measured value 53a. Moreover, the mobile phone 100 acquires information related to the features on the appearance of the activity meter 50 including the measured value 52a and the measured value 53a. For example, a shape 50a of the activity meter 50, a color of the activity meter 50, a position of the indicator 51, a character style and layout of the information displayed in the indicator 51, characters forming the model number 54, a character style and position of the model number 54, and shapes and positions of the buttons 55 and 56 are acquired as the information related to the features on the appearance.

The mobile phone 100 checks the acquired pieces of information against at least one of the used device information 9X and the determination information 9Y, to thereby determine that the measured value 52a indicates steps and the measured value 53a indicates consumed calorie. The mobile phone 100 then acquires the steps and the consumed calorie as numerical value data through the character recognition processing. Timing at which the mobile phone 100 determines that the measured value 52a indicates the steps and the measured value 53a indicates the consumed calorie may be after the character recognition processing is performed.

Figure 6:
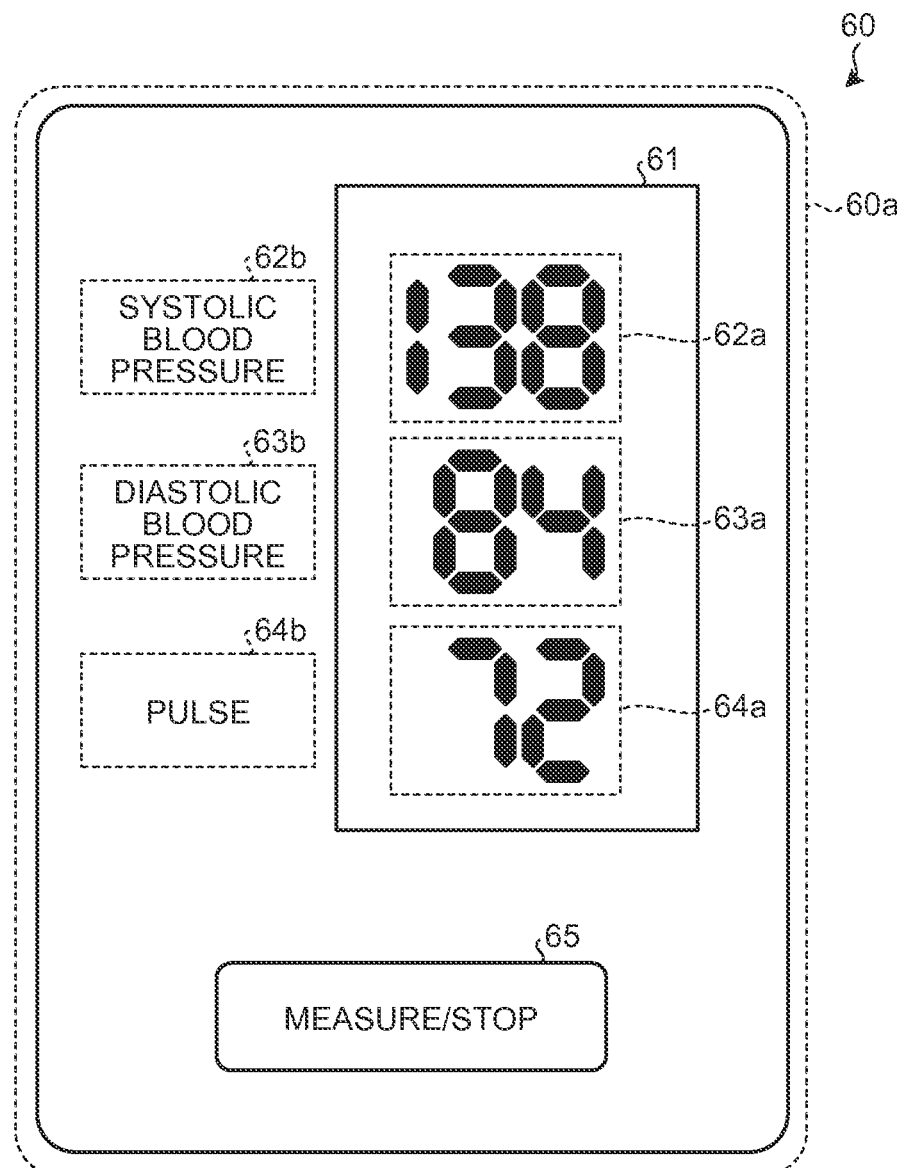
FIG. 6 is a diagram of one of examples of a blood pressure monitor included in an image.

FIG. 6 is a diagram of one of examples of a blood pressure monitor 60 included in an image captured by the camera 13. The blood pressure monitor 60 includes an indicator 61 and a button 65. A measured value 62a indicating systolic blood pressure, a measured value 63a indicating diastolic blood pressure, and a measured value 64a indicating pulses are displayed in the indicator 61. Furthermore, a name 62b representing that the measured value 62a indicates the systolic blood pressure is printed adjacently on the left side of the measured value 62a, a name 63b representing that the measured value 63a indicates the diastolic blood pressure is printed adjacently on the left side of the measured value 63a, and a name 64b representing that the measured value 64a indicates the pulses is printed adjacently on the left side of the measured value 64a.

When the blood pressure monitor 60 as described above is included in the image, the mobile phone 100 detects the measured value 62a, the measured value 63a, and the measured value 64a which are numerical values, the name 62b adjacent to the measured value 62a, the name 63b adjacent to the measured value 63a, and the name 64b adjacent to the measured value 64a. Moreover, the mobile phone 100 acquires information related to the features on the appearance of the blood pressure monitor 60 including the measured value 62a, the measured value 63a, and the measured value 64a. For example, a shape 60a of the blood pressure monitor 60, a color of the blood pressure monitor 60, a position of the indicator 61, a character style and layout of the information displayed in the indicator 61, characters forming each of the names 62b to 64b, a character style and position of each of the names 62b to 64b, and a shape and position of the button 65 are acquired as the information related to the features on the appearance.

The mobile phone 100 checks the acquired pieces of information against at least one of the used device information 9X and the determination information 9Y, to thereby determine that the measured value 62a indicates systolic blood pressure, the measured value 63a indicates diastolic blood pressure, and the measured value 64a indicates pulses. The mobile phone 100 then acquires the systolic blood pressure, the diastolic blood pressure, and the pulses as numerical value data through the character recognition processing.

Figure 7:
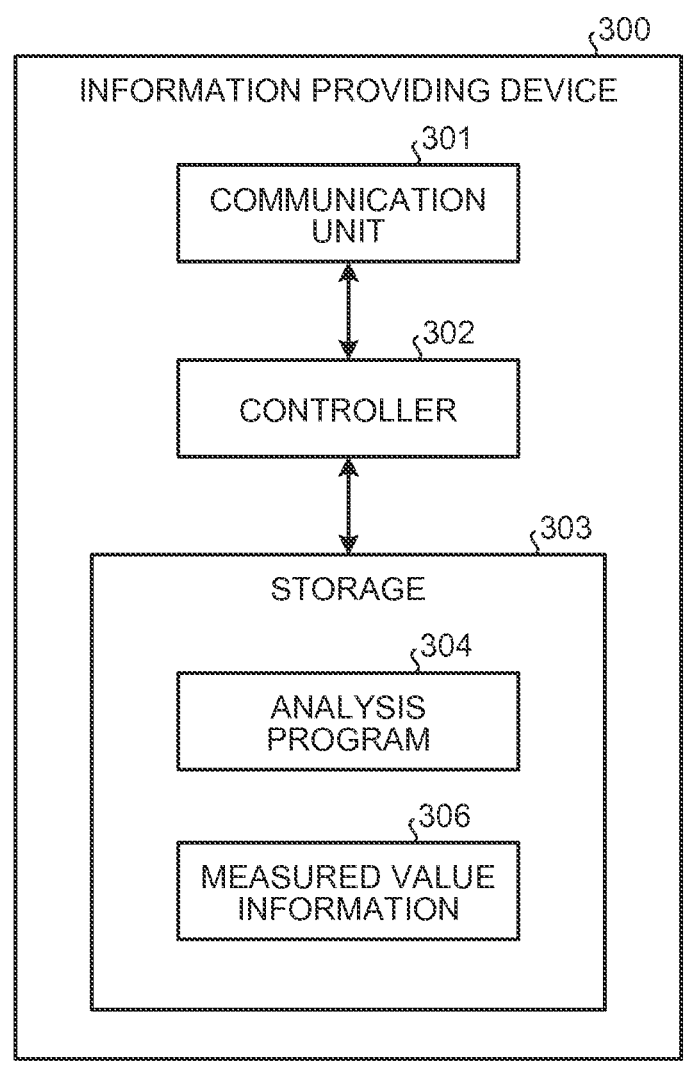
FIG. 7 is a block diagram of an information providing device.

A configuration of the information providing device 300 will be explained with reference to FIG. 7 and FIG. 8. FIG. 7 is a block diagram of the information providing device 300. FIG. 8 is a diagram of one of examples of measured value information. As illustrated in FIG. 7, the information providing device 300 includes a communication unit 301, a controller 302, and a storage 303. The communication unit 301 allows the information providing device 300 to communicate with other devices based on a predetermined protocol.

The controller 302 is a processing unit such as a CPU (Central Processing Unit). The controller 302 integrally controls the operations of the information providing device 300 to implement the various functions. Specifically, the controller 302 executes instructions included in the program stored in the storage 303 while referring to the data stored in the storage 303 as necessary. The controller 10 then executes various information processing according to the data and the instructions.

The controller 302 performs, for example, an analysis program 304 to thereby perform analysis processing based on the stored measured values.

The storage 303 stores therein programs and data. The storage 303 is used also as a work area that temporarily stores a processing result of the controller 302. The storage 303 may include any non-transitory storage medium such as a semiconductor storage medium and a magnetic storage medium. The storage 303 may include a plurality of types of storage mediums. The storage 303 may include a combination of a portable storage medium such as a memory card, an optical disc, or a magneto-optical disc with a reader of the storage medium. The storage 303 may include a storage device used as a temporary storage area such as RAM (Random Access Memory).

The storage 303 stores, for example, the analysis program 304 and measured value information 306. The analysis program 304 provides a function for performing the analysis processing based on the stored measured values.

The measured values transmitted from the mobile phone 100 are accumulated in the measured value information 306. FIG. 8 depicts one of examples of the measured value information 306. As illustrated in FIG. 8, the measured value information 306 includes items such as user ID, timestamp, and type, and a plurality of items in which a measured value and a name of its type are stored in association with each other. Stored in the item of the user ID is an identifier to identify the user of the mobile phone 100. Stored in the item of the timestamp is a date and time when the measured value is read, a date and time when the measured value is transmitted, or a date and time when the measured value is received. Stored in the item of the type is a value indicating the type of the healthcare device from which the measured value is read.

As the example illustrated in FIG. 8, the measured value information 306 is structured so that a plurality of types of measured values can be stored in chronological order. Therefore, the information providing device 300 can perform a high-level analysis related to health based on chronological changes in a plurality of types of measured values.

Figure 9:
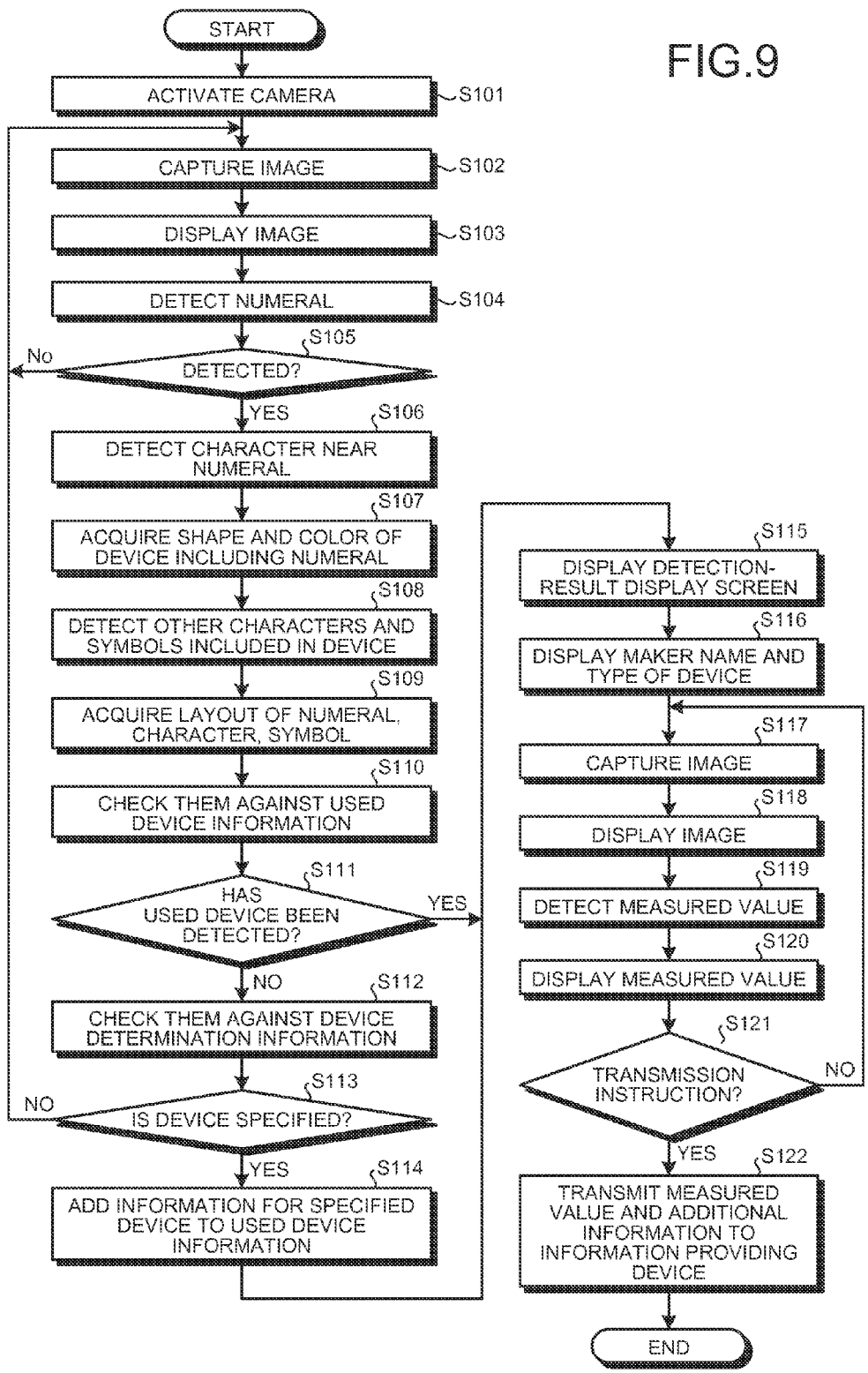
FIG. 9 is a flowchart of a processing procedure for reading and transmitting a measured value.
Figure 10:
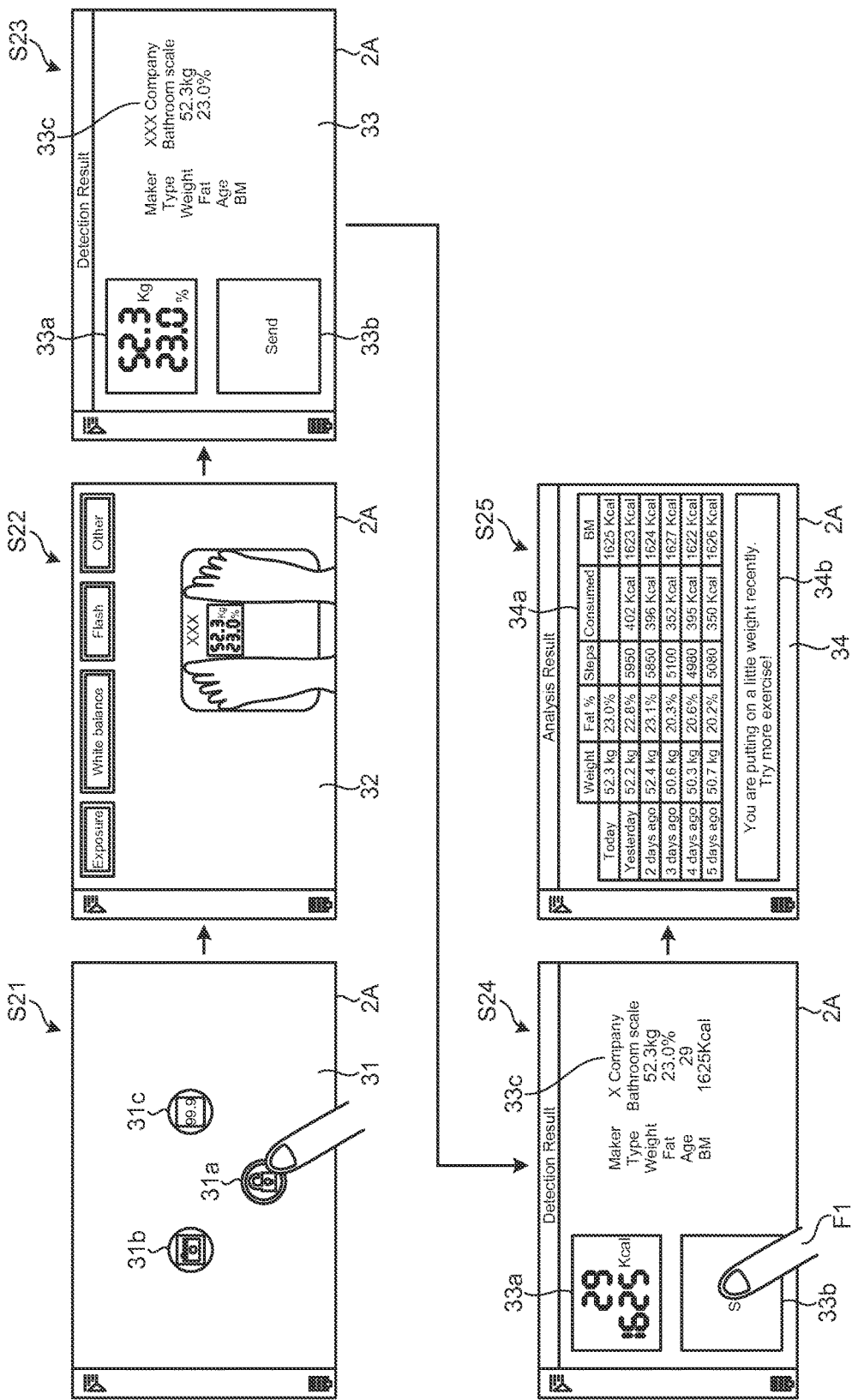
FIG. 10 is a diagram of one of examples of screen transition.

A processing procedure of the mobile phone 100 that reads and transmits a measured value will be explained with reference to FIG. 9 and FIG. 10. FIG. 9 is a flowchart of a processing procedure for reading and transmitting a measured value. FIG. 10 is a diagram of one of examples of screen transition of when the measured value is read and transmitted. The operations illustrated in FIG. 9 and FIG. 10 are implemented by the controller 10 executing the healthcare application 9D.

To perform the procedure illustrated in FIG. 9, first of all, the controller 10 activates the healthcare application 9D. The activation of the healthcare application 9D is performed in response to, for example, detection of a user operation. The operation to activate the healthcare application 9D may be an operation performed on a menu or an operation performed on an icon similarly to the operation to activate other applications. Alternatively, the operation to activate the healthcare application 9D may be an operation on a lock screen.

The lock screen is a screen on which an operation for shifting the mobile phone 100 from a standby state to a normal state. At Step S21 illustrated in FIG. 10, a lock screen 31 is displayed on the display 2A. An unlock icon 31a, a camera icon 31b, and a measured value reading icon 31c are laid out on the lock screen 31.

When an operation of moving the unlock icon 31a in the direction of the camera icon 31b with a flick or a drag is detected through the touch screen 2B, the controller 10 activates an application for photography. When an operation of moving the unlock icon 31a in the direction of the measured value reading icon 31c with a flick or a drag is detected through the touch screen 2B, the controller 10 activates the healthcare application 9D. When an operation of moving the unlock icon 31a in any other direction with a flick or a drag is detected through the touch screen 2B, the controller 10 displays a home screen or a screen displayed before the shift to the standby state on the display 2A.

By configuring so that the healthcare application 9D can be activated by an operation performed on the lock screen in this way, the user can rapidly start read of the measured value from the healthcare device.

When the healthcare application 9D is activated, the controller 10 first activates the camera 13 (Step S101), as illustrated in FIG. 9. Then, the controller 10 captures an image using the camera 13 (Step S102), and displays the captured image on the display 2A (Step S103).

At this stage, as illustrated at Step S22 in FIG. 10, an image capture screen 32 for capturing an image is displayed on the display 2A. When the user standing on the body composition meter directs the camera 13 toward the body composition meter, the body composition meter displaying the body weight and the body fat percentage in the indicator is captured, as illustrated at Step S22.

Subsequently, the controller 10 detects a numeral in the image captured by the camera 13 (Step S104). When the numeral cannot be detected in the image, that is, when the healthcare device that displays the measured value is not captured (No at Step S105), the controller 10 re-executes Step S102 and subsequent steps.

When the numeral in the image captured by the camera 13 can be detected (Yes at Step S105), the controller 10 detects characters near the numeral (Step S106). Moreover, the controller 10 acquires the shape and the color of the device including the numeral (Step S107), and detects other characters and symbols included in the device (Step S108). The controller 10 then acquires a layout of the detected numeral, characters, and symbols (Step S109). The order of Steps S106 to S108 is not limited thereto.

After the information related to the features on the appearance of the healthcare device is acquired in this way, the controller 10 checks the acquired information against the used device information 9X (Step S110). When there is a healthcare device whose matching degree of the information related to the features on the appearance is higher than a predetermined value, that is, when the used device in the image is detected (Yes at Step S111), the controller 10 executes Step S115 and subsequent steps.

When the used device in the image is not detected (No at Step S111), the controller 10 checks the acquired information related to the features on the appearance of the healthcare device against the determination information 9Y in order to detect a healthcare device other than the used device (Step S112). When the healthcare device in the image cannot be specified through checking (No at Step S113), the controller 10 re-executes Step S102 and subsequent steps.

When the healthcare device in the image can be specified through checking (Yes at Step S113), the controller 10 adds the information of the specified healthcare device to the used device information 9X (Step S114). Specifically, the information related to the features on the appearance acquired at Step S104 to Step S109 is added to the used device information 9X in association with the information indicating the position and type of measured value of the data in the determination information 9Y corresponding to the healthcare device specified at Step S113. In this way, by storing the information for the newly recognized healthcare device in the used device information 9X, the processing related to the healthcare device is speeded up at the next and subsequent times. Thereafter, the controller 10 executes Step S115 and subsequent steps.

At Step S115, the controller 10 displays a detection-result display screen on the display 2A (Step S115). The controller 10 then displays the maker name and the type of the healthcare device included in the captured image on the detection-result display screen (Step S116).

Subsequently, the controller 10 captures an image using the camera 13 (Step S117), and displays the captured image on the detection-result display screen (Step S118). The controller 10 then detects the measured values in the image (Step S119), and displays the detected measured values on the detection-result display screen (Step S120).

At this stage, for example, a detection-result display screen 33 as illustrated at Step S23 in FIG. 10 is displayed on the display 2A. The detection-result display screen 33 includes an image display area 33a, a send button 33b, and a detection-result display area 33c. The image display area 33a is an area in which the captured image is displayed. The controller 10 enlarges an area, of the captured image, where the measured values are displayed, and displays the enlarged area in the image display area 33a. Therefore, the user can easily grasp the measured values even in such a situation that the indicator of the healthcare device cannot be seen well. The mobile phone 100 may be configured such that the user can correct the detection result using the touch screen 2B or the button 3 at Step S120.

The send button 35 is a button for instruction of executing transmission of the measured values and the additional information to the information providing device 300. The detection-result display area 33c is an area in which the information obtained by analyzing the captured image is displayed.

Subsequently, the controller 10 determines whether transmission of the measured values and the additional information has been instructed (Step S121). When transmission has not been instructed (No at Step S121), the controller 10 re-executes Step S117 and subsequent steps. In this way, the controller 10 repeats acquisition of an image, display of the image, detection of measured values, and display of the detected values until the transmission is instructed. Therefore, when a measured value included in the image is changed, the mobile phone 100 can reflect the change in the detection result.

For example, in the case of the body composition meter, it may take some time until the measured values are stabilized. Even in this case, the controller 10 repeatedly performs the detection of measured values, and can therefore reflect the latest measured value in the detection result. Moreover, in the case of the body composition meter, the type of the measured value displayed in the indicator may be changed according to a user's operation or according to passage of time. Even in this case, the controller 10 repeatedly performs detection of measured values, and can therefore reflect the newly displayed measured value in the detection result as illustrated at Step S24 in FIG. 10. To determine the type of the newly displayed measured value, the controller 10 may perform detection of a character or symbol near the measured value and check of the detected character or symbol against the determination information 9Y, at Step S 119.

Furthermore, the controller 10 repeatedly performs processing of enlarging the area, of the captured image, where the measured values are displayed and displaying the enlarged area in the image display area 33a, and therefore the same portion in the image can be continuously displayed even if the image is blurred due to camera shake. Thus, the mobile phone 100 can enhance the visibility of the displayed image.

Moreover, because the analysis of the image is repeatedly performed, the user can also perform the operation of causing the mobile phone 100 to read the model number of the healthcare device to fix the type of the healthcare device and the position and type of the measured value displayed in the indicator of the healthcare device, and then causing the mobile phone 100 to read the measured value.

When the transmission has been instructed (Yes at Step S121), the controller 10 instructs the communication unit 6 to transmit the detected measured value and the additional information to the information providing device 300 (Step S122). The transmission is instructed by, for example, the user, who checks the measured value displayed on the detection-result display screen 33, tapping the send button 33b using a finger F1 as illustrated at Step S24 in FIG. 10.

Thereafter, when the analysis result is transmitted from the information providing device 300, the controller 10 displays the analysis result on the display 2A. For example, the controller 10 displays, for example, an analysis result screen 34 illustrated at Step S25 in FIG. 10 on the display 2A. The analysis result screen 34 includes a history display area 34a for displaying chronological changes in a plurality of types of measured values, and an advice display area 34b for displaying an advice obtained by analysis processing.

The embodiments disclosed in the present application can be modified within a range not departing from the gist and the scope of the invention. Moreover, the embodiments and the modifications thereof disclosed in the present application can be appropriately combined with each other. For example, the embodiment may be modified as follows.

For example, each of the programs illustrated in FIG. 3 and FIG. 7 may be divided into a plurality of modules or may be combined with another program.

The arrangement of the functions of the mobile phone 100 and the function of the information providing device 300 may be appropriately changed. For example, the mobile phone 100 may perform the functions of the information providing device 300. That is, the mobile phone 100 may accumulate and analyze the measured values in addition to reading the measured value.

Figure 11:
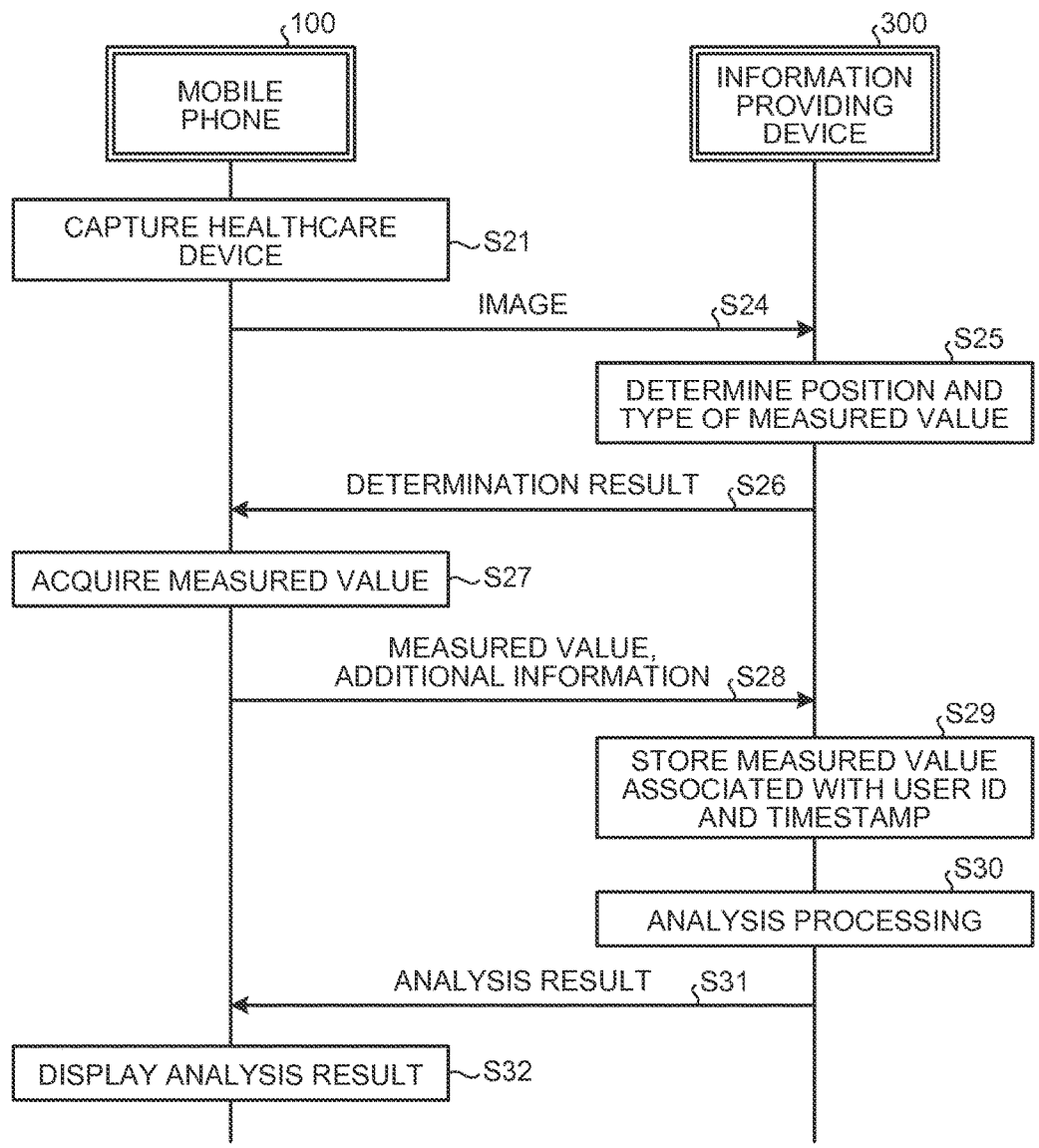
FIG. 11 is a diagram of a modification of the operation of the information providing system.
Figure 12:
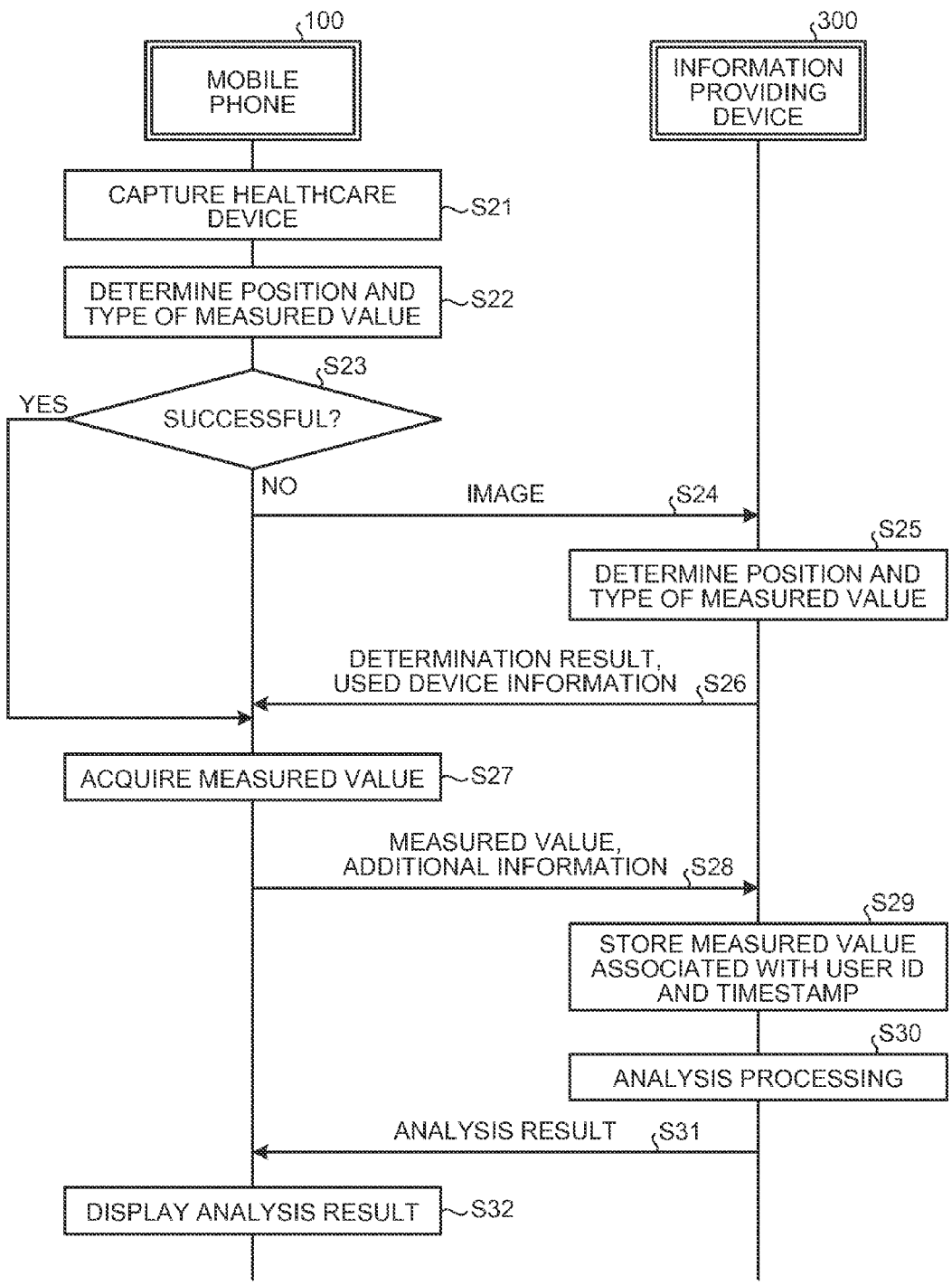
FIG. 12 is a diagram of another modification of the operation of the information providing system.

Alternatively, the information providing device 300 may perform part of the functions of the mobile phone 100. When the information providing device 300 performs part of the functions of the mobile phone 100, the processing of determining the position and type of the measured value included in the image may be performed by the information providing device 300. In this case, as illustrated in FIG. 11, it may be configured such that the mobile phone 100 transmits the image to the information providing device 300, and the information providing device 300 performs both the checking of the image against the used device information 9X and the checking thereof against the determination information 9Y. FIG. 11 is a diagram of a modification of the operation of the information providing system. Alternatively, as illustrated in FIG. 12, it may be configured such that the mobile phone 100 checks the image against the used device information 9X and transmits the image to the information providing device 300 when the position and the like of the measured value cannot be determined, and the information providing device 300 checks the image against the determination information 9Y. FIG. 12 is a diagram of another modification of the operation of the information providing system. In the example illustrated in FIG. 12, the information providing device 300 transmits a determination result and the used device information 9X corresponding to the determination result to the mobile phone 100; however, it may be configured to transmit only the determination result. In the configuration illustrated in FIG. 11, the load on the mobile phone 100 is reduced and the support of a new model of the healthcare device is facilitated. In the configuration illustrated in FIG. 12, it is possible to reduce the time required for determination of the position and the like of the measured value while facilitating the support of a new model of the healthcare device.

Figure 13:
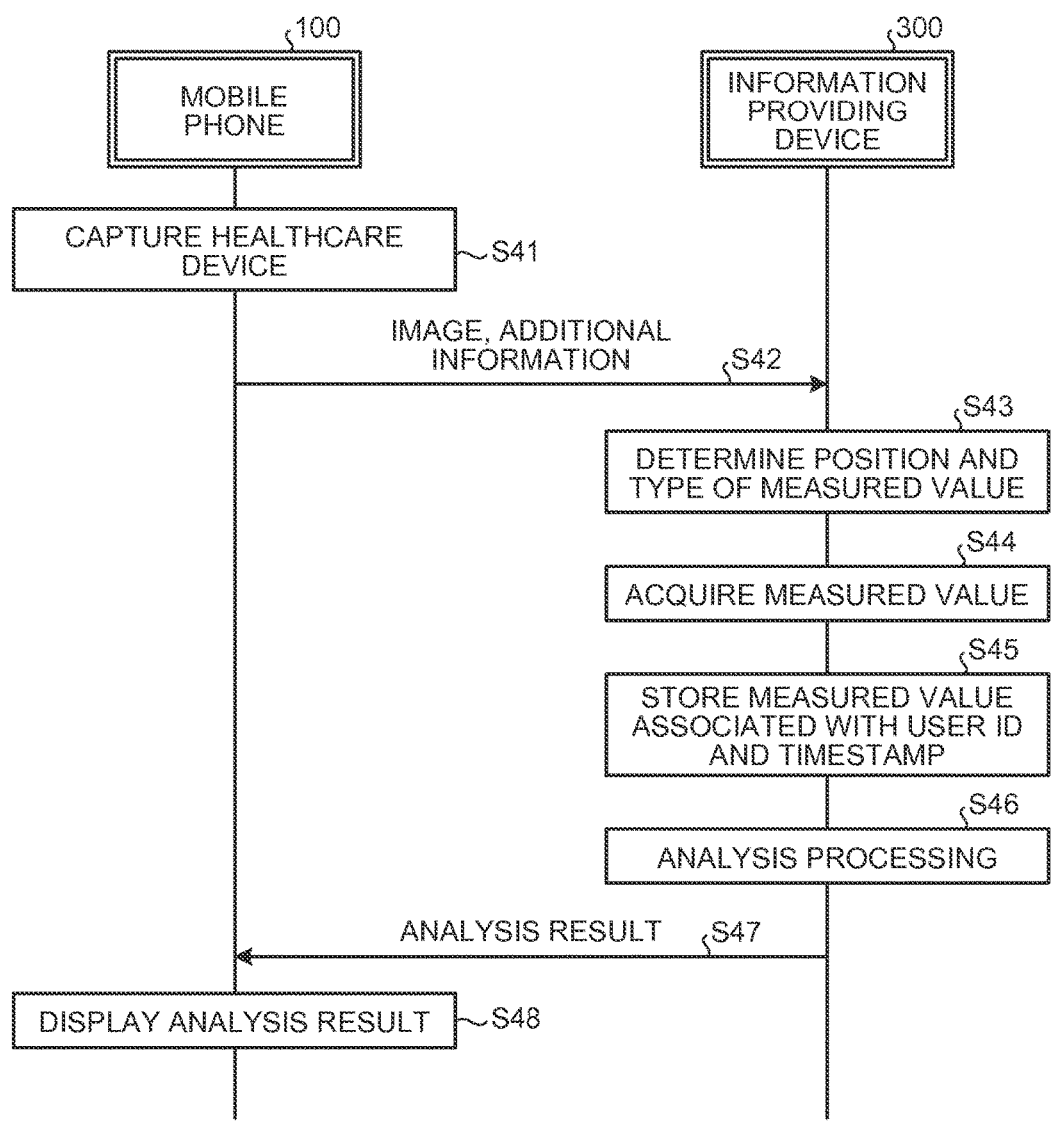
FIG. 13 is a diagram of another modification of the operation of the information providing system.

When part of the functions of the mobile phone 100 is performed by the information providing device 300, it may be configured such that the mobile phone 100 transmits the image and the additional information to the information providing device 300, and the information providing device 300 reads the measured value in addition to determining the position and the like of the measured value, as illustrated in FIG. 13. FIG. 13 is a diagram of another modification of the operation of the information providing system. In the configuration illustrated in FIG. 13, the load on the mobile phone 100 can be further reduced.

Figure 14:
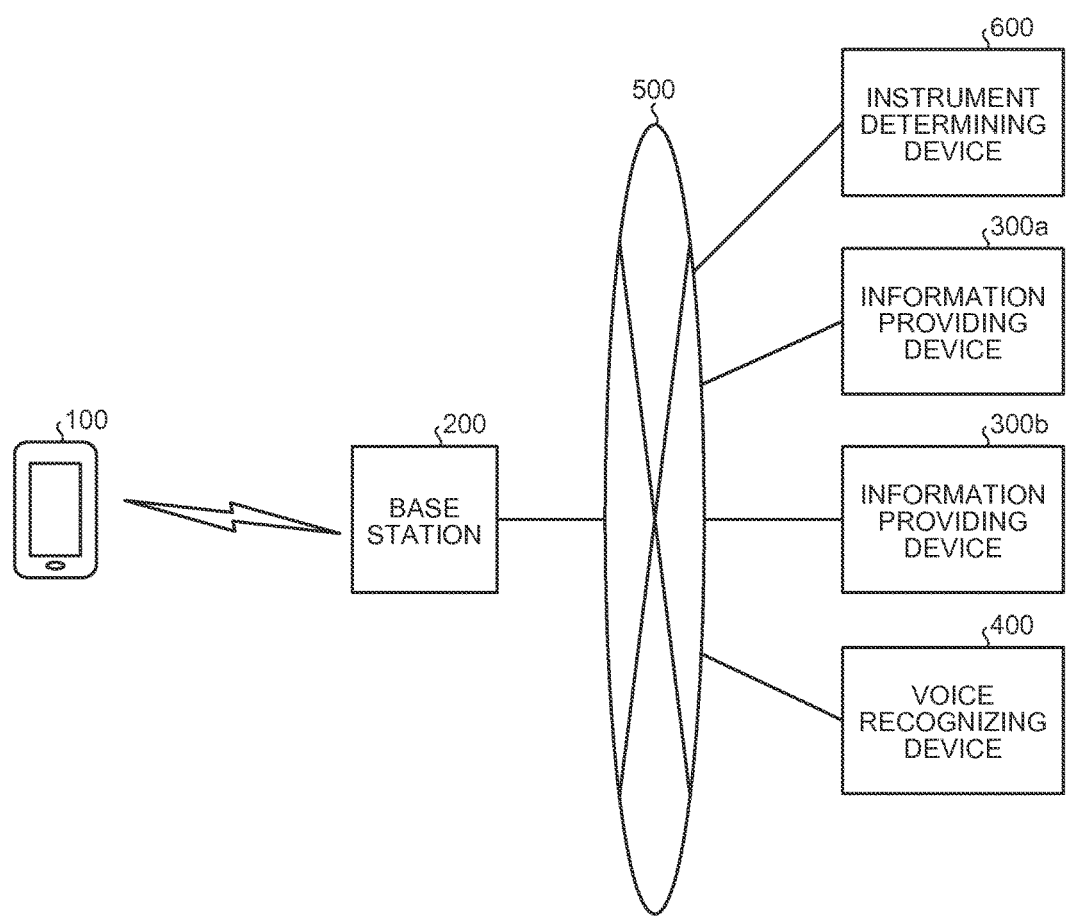
FIG. 14 is a diagram of another configuration of the information providing system.

Alternatively, part of the functions of the mobile phone 100 may be performed by a device other than the information providing device 300. For example, as illustrated in FIG. 14, an instrument determining device 600 for determining a position and the like of a measured value may be added to the information providing system. FIG. 14 is a diagram of another configuration of the information providing system.

The embodiment has explained the examples in which the mobile phone 100 reads the measured value displayed in the indicator of the healthcare device; however, the way to read the measured value is not limited thereto. For example, the mobile phone 100 may read a measured value from a positional relation between a pointer and a scale provided in an analog healthcare device.

When reading a measured value of a measuring instrument such as a bathroom scale or a body composition meter for measuring body weight, the user is thought to step on the measuring instrument while holding the mobile phone 100. Therefore, to remove the influence which the weight of the mobile phone 100 exerts on the measured value, the mobile phone 100 may be configured such that the weight of the mobile phone 100 is stored therein in advance and the weight of the mobile phone 100 is removed from the measured value indicating the body weight when the device displaying the measured value is a measuring instrument for measuring body weight.

The healthcare device may be configured such that the measured value is displayed not only as a numerical value but also as a code that the mobile phone 100 can easily read. In this case, the type, the unit, and the like of the measured value may be encoded, as well as the measured value. The encoding can be implemented by using, for example, a one-dimensional barcode or a two-dimensional barcode. Alternatively, when the indicator of the healthcare device uses a 7-segment display, the encoding may be implemented by assigning a flashing pattern of elements forming each character to a code.

When user's personal information such as age, height, and gender is registered in the healthcare device, the healthcare device may be configured in such a manner as to display not only the measured value but also the personal information in the indicator. By such a configuration, the mobile phone 100 acquires personal information not registered in the mobile phone 100 from the healthcare device and transmits the acquired personal information to the information providing device 300, so that the information can be used for analysis. The personal information may be displayed as text in the indicator of the healthcare device or may be displayed by being encoded in the above manner. The personal information may be stored in the information providing device 300 in advance.

The mobile phone 100 may perform control so that an orientation of an image obtained by capturing the indicator is changed according to an aspect ratio of the indicator of the healthcare device. A relationship between an aspect ratio of the indicator and an aspect ratio of the image will be explained using a case of capturing the indicator 41 of the body composition meter 40 illustrated in FIG. 4 as one of examples. In the following explanation, a match between the orientation of the indicator of the healthcare device and the orientation of the captured image means a match between a long-side direction of the indicator and a long-side direction of the image (a match between a short-side direction of the indicator and a short-side direction of the image). The match between the orientation of the indicator of the healthcare device and the orientation of the captured image may be meant that an orientation of a measured value displayed in the indicator and of a character or symbol etc. near the measured value matches the short-side direction of the image.

FIG. 15 is a diagram of one of examples of when the indicator 41 of the body composition meter 40 is captured under a light source. In the example illustrated in FIG. 15, a light source L1 is provided on a ceiling and the body composition meter 40 is placed on a floor. The mobile phone 100 is held by the user in between the light source L1 and the body composition meter 40 in order to capture the indicator 41 of the body composition meter 40 using the camera 13. In this case, a shadow of the mobile phone 100 occurs over the body composition meter 40 due to the light from the light source L1, and the shadow is likely to unexpectedly appear in the image captured by the camera 13. In the description herein below, for the sake of simplicity, a user's body (especially, hand) by which the mobile phone 100 is held is not considered.

Figure 16:
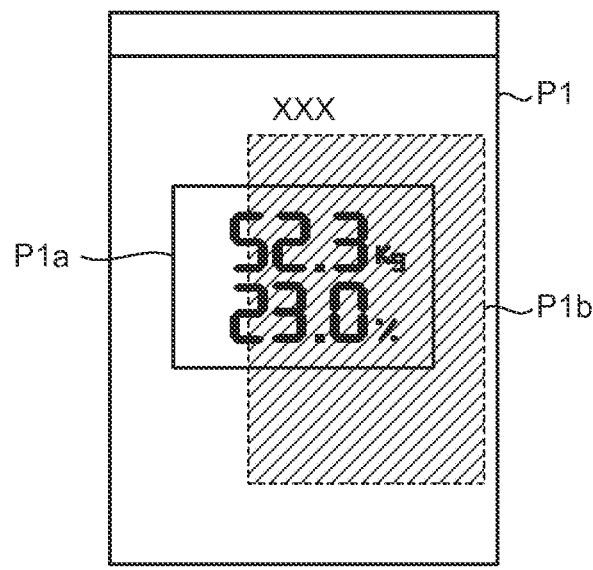
FIG. 16 is a diagram of one of examples of an image in which a shadow of the mobile phone unexpectedly appears.

FIG. 16 is a diagram of one of examples of an image in which the shadow of the mobile phone 100 unexpectedly appears. A picture image P1 illustrated in FIG. 16 is captured in an orientation different from that of the indicator 41. That is, the picture image P1 illustrated in FIG. 16 is captured in an orientation in which a long-side direction of the picture image P1 does not match the long-side direction of the indicator 41 (in an orientation in which a short-side direction of the picture image P1 does not match the short-side direction of the indicator 41). Therefore, an orientation of an image P1a of the indicator 41 in the picture image P1 does not match the orientation of the picture image P1.

A shadow P1b of the mobile phone 100 unexpectedly appears in the picture image P1. The mobile phone 100 is configured such that the touch screen display 2 thereof is provided over a substantially entire surface of the face opposite to the camera 13 and an image being captured by the camera 13 can be displayed on the substantially entire surface of itself. Therefore, the orientation of the image captured by the camera 13 matches the orientation of the mobile phone 100, and thus the orientation of the shadow P1b of the mobile phone 100 in the picture image P1 is always the same as the orientation of the picture image P1.

In this way, the picture image P1 includes the image P1a of the indicator 41 in the orientation different from that of the picture image P1 and the shadow P1b in the same orientation as that of the picture image P1. The images in the different orientations in the above manner are likely to have a relationship in which only parts of them overlap each other as the example illustrated in FIG. 16. When the shadow P1b overlaps part of the image P1a in this manner, the luminance and the like inside the image P1a partially change, and the partial change may adversely affect the reading of the measured value in the image P1a. Particularly, when a reflective display panel without a backlight is used for the indicator of the healthcare device, an amount of change in the luminance of the indicator is originally small, and therefore the measured value may become difficult to be read due to a luminance difference produced by the shadow.

Figure 17:
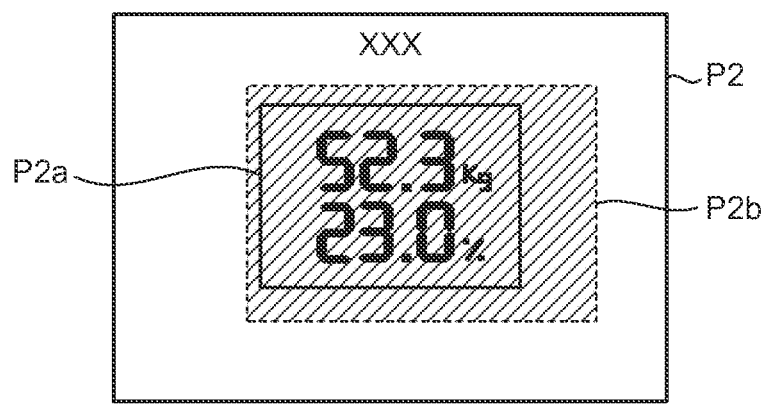
FIG. 17 is a diagram of another example of the image in which the shadow of the mobile phone unexpectedly appears.

FIG. 17 is a diagram of another example of an image in which the shadow of the mobile phone 100 unexpectedly appears. A picture image P2 illustrated in FIG. 17 is captured in the same orientation as that of the indicator 41. That is, the picture image P2 illustrated in FIG. 17 is captured in an orientation in which a long-side direction of the picture image P2 matches the long-side direction of the indicator 41 (in an orientation in which a short-side direction of the picture image P2 matches the short-side direction of the indicator 41). Therefore, an orientation of an image P2a of the indicator 41 in the picture image P2 matches the orientation of the picture image P2.

A shadow P2b of the mobile phone 100 unexpectedly appears in the picture image P1. As explained above, the orientation of the image captured by the camera 13 matches the orientation of the mobile phone 100. Therefore, the orientation of the shadow P2b of the mobile phone 100 in the picture image P2 matches the orientation of the picture image P2.

In this way, the picture image P2 includes the image P2a of the indicator 41 in the same orientation as that of the picture image P2 and the shadow P2b in the same orientation as that of the picture image P2. The images in the same orientations in the above manner are likely to have a relationship in which one is included in the other, as the example illustrated in FIG. 17. Moreover, in consideration of a general size of the indicator of the healthcare device, a general size of the mobile phone, a relative positions between the light source, the mobile phone, and the healthcare device in a room as generally assumed, and the like, it is considered that the shadow P2b is, in many cases, larger than the image P2a of the indicator 41. Therefore, when the picture image P2 is captured in the same orientation as that of the indicator 41, a relationship in which the image P2a of the indicator 41 is included in the shadow P2b is likely to be made, as the example illustrated in FIG. 17. In such a relationship as above, a difference in the luminance or the like due to the shadow P2b is not produced inside the image P2a of the indicator 41, and therefore the influence of the shadow P2b exerted on the reading of the measured value is small even if the shadow P2b unexpectedly appears in the image P2a.

Figure 18:
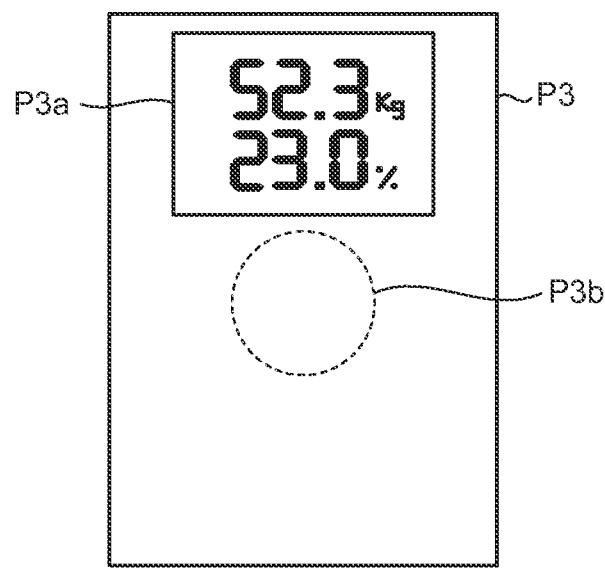
FIG. 18 is a diagram of one of examples of an image captured in an orientation different from that of an indicator.

A portion in which photometric processing is performed to adjust exposure (automatic exposure, automatic sensitivity adjustment) may affect the reading of the measured value as well as the change of the luminance or the like due to the shadow. When the orientation of the indicator of the healthcare device is different from the orientation of a captured image, the entire indicator can be captured even if the position of the indicator in the picture image is largely displaced from the center of the picture image. FIG. 18 is a diagram of one of examples of an image captured in an orientation different from that of the indicator. In a picture image P3 illustrated in FIG. 18, an image P3a of the indicator 41 includes the entire indicator 41 but is largely displaced from the center of the picture image P3. Accordingly, when the mobile phone 100 performs photometric processing based on a central area P3b as a default operation, exposure adjustment is performed based on brightness in an area not including the image P3a of the indicator 41, and therefore it may become difficult to read the measured value in the image P3a of the indicator 41.

For example, when a color in the portion of the body composition meter 40 corresponding to the area P3b is white, the entire captured image becomes dark, which is likely to cause underexposure of the measured value in the image P3a of the indicator 41. Alternatively, when a color in the portion of the body composition meter 40 corresponding to the area P3b is black, the entire captured image becomes bright, which is likely to cause overexposure of the measured value in the image P3a of the indicator 41.

Figure 19:
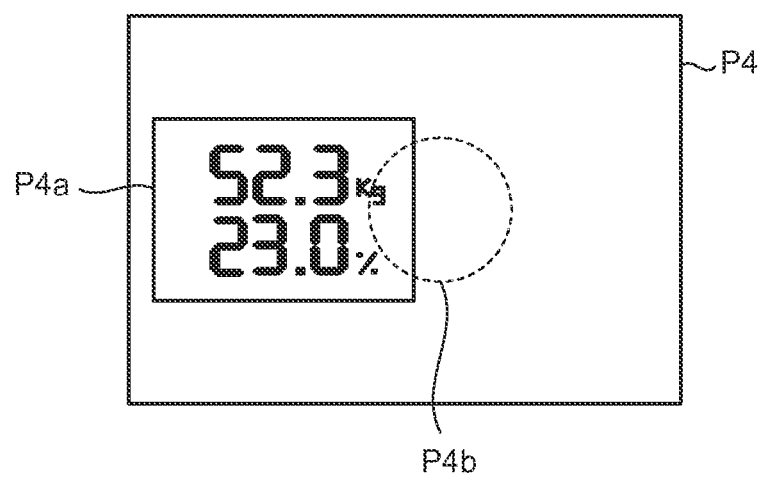
FIG. 19 is a diagram of one of examples of an image captured in the same orientation as that of an indicator.

On the other hand, when the orientation of the indicator of the healthcare device is the same as the orientation of a captured image, the position of the image of the indicator the whole of which is captured is hardly displaced largely from the center of the captured image. FIG. 19 is a diagram of one of examples of an image captured in the same orientation as that of the indicator. In a picture image P4 illustrated in FIG. 19, an image P4a of the indicator 41 includes the entire indicator 41. In the picture image P4, the image P4a of the indicator 41 has substantially the same size as that of the image P3a of the indicator 41 in FIG. 18, and the image P4a appears in a position largely displaced to the left from the center of the picture image P4. However, the right edge of the image P4a is located at substantially the center of the picture image P4. Accordingly, when the mobile phone 100 performs the photometric processing based on a central area P4b as a default operation, exposure adjustment is performed based on the brightness of an area including the image P4a of the indicator 41, and therefore the picture image P4 suitable for reading the measured value in the image P4a of the indicator 41 is obtained.

By matching an orientation of a captured image and an orientation of an indicator of a healthcare device included in the image, it is possible to increase the possibility of obtaining an image suitable for reading the measured value. For example, when capturing of the indicator of the healthcare device and analysis of the captured image are repeatedly performed until the measured value is successfully read from the healthcare device, matching the orientation of the image and the orientation of the indicator of the healthcare device enables the system to shorten the time required to succeed at reading the measured value.

Figure 20:
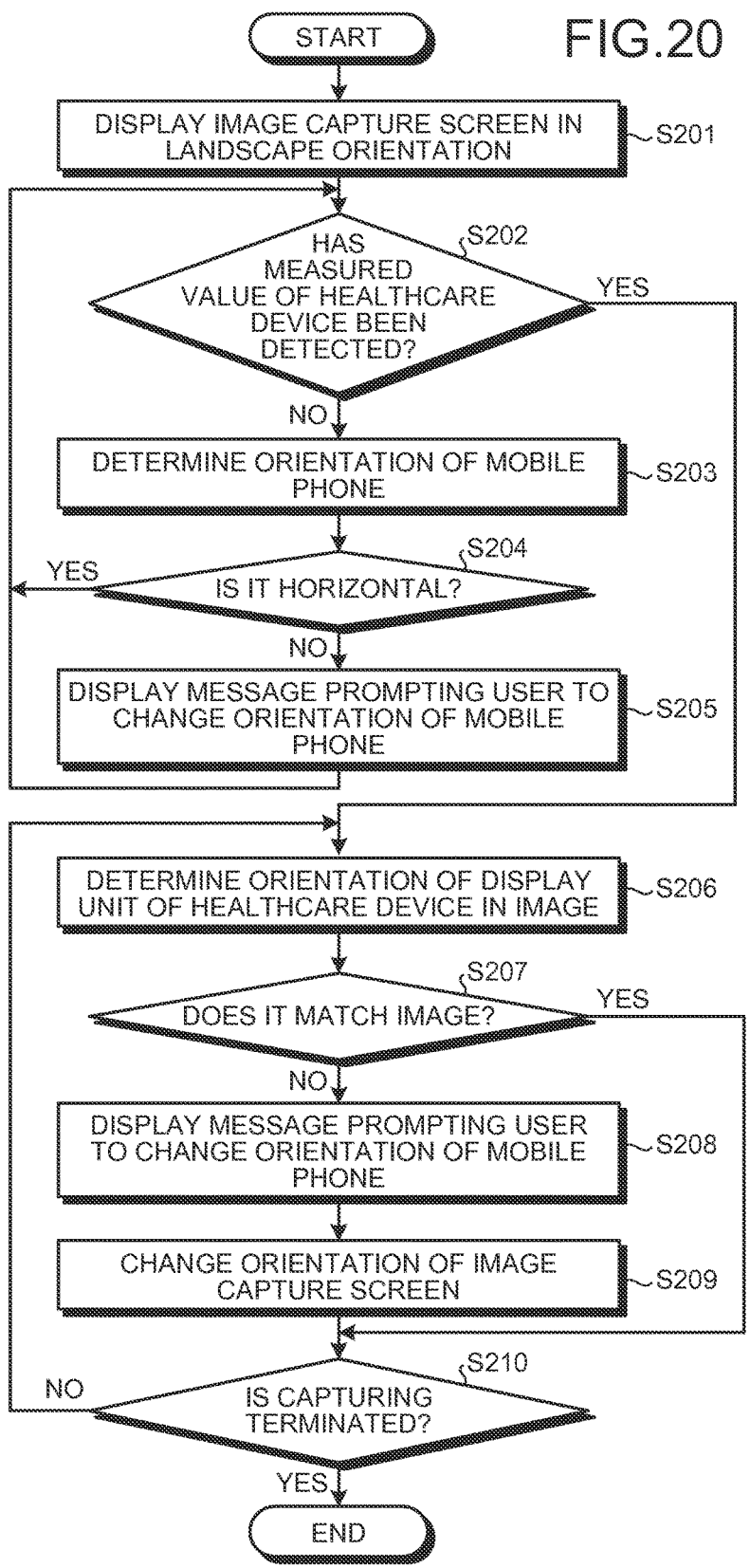
FIG. 20 is a flowchart of one of examples of control for matching an orientation of a captured image and an orientation of an indicator of a healthcare device included in the image.

The control for matching an orientation of a captured image and an orientation of an indicator of a healthcare device included in the image will be explained with reference to FIG. 20. FIG. 20 is a flowchart of one of examples of the control for matching the orientation of a captured image and the orientation of the indicator of a healthcare device included in the image. The control illustrated in FIG. 20 is implemented by the controller 10 executing the healthcare application 9D. The control illustrated in FIG. 20 is performed in parallel to the processing illustrated in FIG. 9.

As illustrated in FIG. 20, as an initial operation before the orientation of the indicator of a healthcare device is determined, the controller 10 performs control based on an assumption that the orientation of the indicator of the healthcare device is horizontal. This is because the orientation of the indicator of the healthcare device is in many cases horizontal. The controller 10 may be configured to perform control based on an assumption that the orientation of the indicator of the healthcare device is vertical, according to the setting or the operation performed by the user.

Specifically, at Step S201, the controller 10 displays an image capture screen to capture the indicator of the healthcare device in landscape orientation. Images captured by the camera 13 are continuously displayed on the image capture screen. Subsequently, at Step S202, the controller 10 determines whether the measured value of the healthcare device has been detected at Step S104 in the processing illustrated in FIG. 9. When the measured value has not been detected (No at Step S202), the controller 10 proceeds to Step S203.

At Step S203, the controller 10 determines the orientation of the mobile phone 100. The orientation of the mobile phone 100 can be determined using a detector such as the acceleration sensor 15 and the gyroscope 17. When the orientation of the mobile phone 100 is horizontal (Yes at Step S204), the controller 10 returns to Step S202.

When the orientation of the mobile phone 100 is not horizontal (No at Step S204), the controller 10 performs the control so as to change the orientation of the mobile phone 100 to the horizontal orientation. Specifically, at Step S205, the controller 10 displays a message prompting the user to change the orientation of the mobile phone 100 on the display 2A. The controller 10 may stop the display of a captured image on the image capture screen in addition to the display of the message. Stopping the display of the image can make the user realize that the orientation of capturing an image is not appropriate. Thereafter, the controller 10 returns to Step S202.

When the measured value of the healthcare device has been detected at Step S104 in the processing illustrated in FIG. 9 (Yes at Step S202), the controller 10 proceeds to Step S206. At Step S206, the controller 10 determines an orientation of the indicator in the image. The orientation determined herein is an orientation determined by the long-side direction and the short-side direction of the indicator, which has no relation with the orientation in which the measured value is displayed. The orientation of the indicator can be determined based on, for example, the shape of the area where the measured value is detected in the processing of FIG. 9, the model of the healthcare device specified in the processing of FIG. 9, and the like.

Subsequently, at Step S207, the controller 10 determines whether the orientation of the indicator of the healthcare device matches the orientation of the image being captured. When the orientation of the indicator matches the orientation of the image being captured (Yes at Step S207), the controller 10 proceeds to Step S210.

When the orientation of the indicator of the healthcare device does not match the orientation of the image being captured (No at Step S207), the controller 10 performs the control so as to match the orientation of the captured image to the orientation of the indicator. Specifically, at Step S208, the controller 10 displays a message prompting the user to change the orientation of the mobile phone 100 on the display 2A, and changes the orientation of the image capture screen at Step S209. An execution order does not matter between Step S208 and Step S209. The controller 10 may stop the display of a captured image on the image capture screen in addition to these controls. Thereafter, the controller 10 proceeds to Step S210.

At Step S210, the controller 10 determines whether the capturing is terminated. When the capturing is not terminated (No at Step S210), the controller 10 returns to Step S206. When the capturing is terminated (Yes at Step S210), the controller 10 ends the processing illustrated in FIG. 20. The controller 10 may always terminate the processing at Step S210.

Embodiment 2

The embodiment 1 has explained the examples in which the mobile phone 100 reads the numerical data corresponding to the measured value through the character recognition processing from the image obtained by capturing the measured value displayed in the indicator of the healthcare device. At this time, any object other than the measured value included in image data (image) captured by the camera 13 affects adjustment of an exposure amount or the like when an image is acquired from the image data. Therefore, variation may occur in precision of measured value read from the image by the mobile phone 100. Particularly, when the indicator of a healthcare device is formed of a 7-segment display that displays a black character on a gray-scale liquid crystal panel, a measured value in an image acquired from the image data becomes obscure depending on a proportion of a white object included in the image data. If the precision of the measured value is low, the information providing device 300 cannot perform correct analysis on a user's health condition, which leads to degradation of service quality related to healthcare. Therefore, one of examples of the control of the mobile phone 100 to precisely read the measured value displayed in the indicator from the image of the captured indicator of the healthcare device will be explained below.

The healthcare application 9D provides functions which will be explained below in addition to the functions explained in the embodiment 1. The healthcare application 9D provides a function of specifying an area in image data, in which an image of the indicator of a healthcare device appears, based on a luminance distribution of the image data for the healthcare device captured by the camera 13. The healthcare application 9D further provides a function of performing photometric processing targeted at the specified area.

The controller 10 executes the healthcare application 9D to thereby specify an area in the image data in which an image of the indicator of the healthcare device appears based on the luminance distribution of the image data for the healthcare device captured by the camera 13. Furthermore, the controller 10 executes the healthcare application 9D to thereby perform the photometric processing targeted at the specified area.

Figure 21:
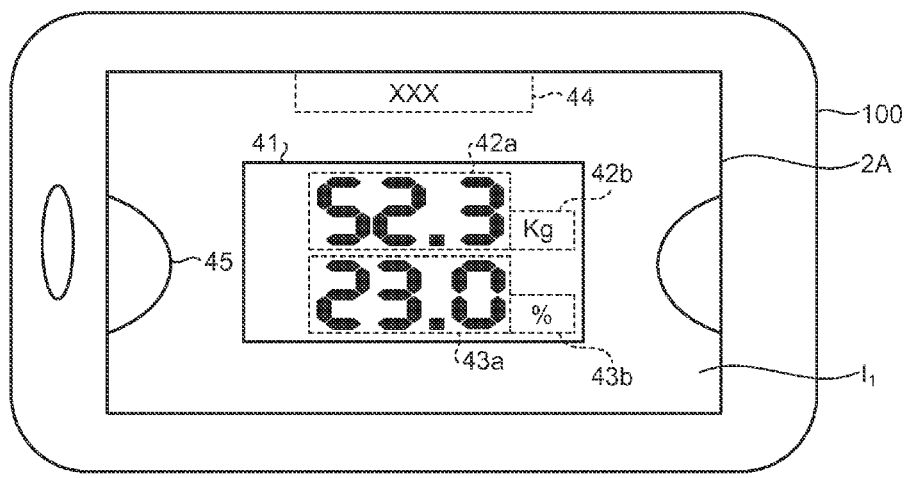
FIG. 21 is a diagram of one of examples of a state in which image data is captured by a camera.

FIG. 21 is a diagram of one of examples of a state in which image data is captured by a camera. FIG. 21 depicts a case where image data for the body composition meter 40 being a healthcare device is captured. The user operates the camera 13 and the mobile phone 100 while checking a situation in which the image data for the indicator 41 of the body composition meter 40 being an object to be captured is displayed on the touch screen display 2 (display 2A). As illustrated in FIG. 21, the controller 10 displays image data $I_1$ for the body composition meter 40 that can be captured by the camera 13 on the display 2A, according to a user's operation.

Figure 22:
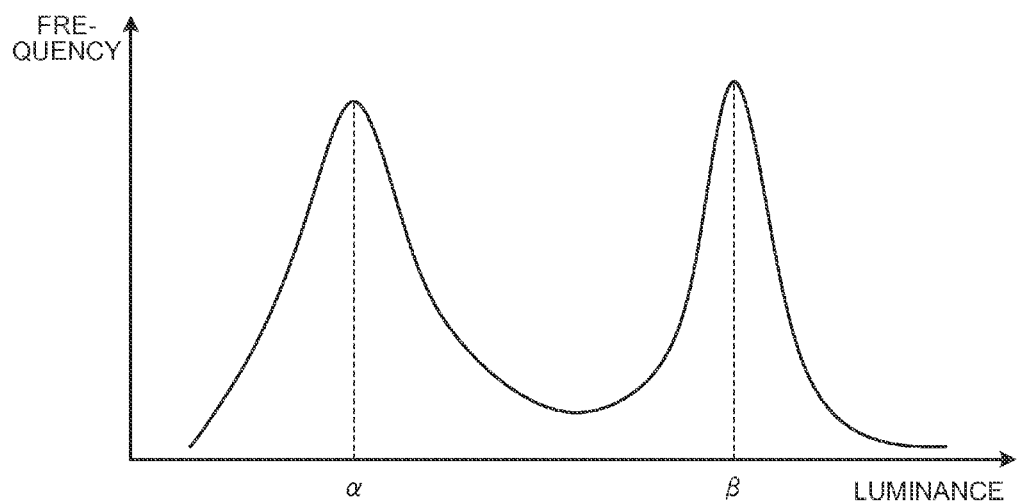
FIG. 22 is a diagram of one of examples of a luminance distribution of the image data illustrated in FIG. 21.

FIG. 22 is a diagram of one of examples of a luminance distribution of the image data illustrated in FIG. 21. A horizontal axis illustrated in FIG. 22 indicates a luminance value and a vertical axis indicates a frequency of the luminance value. The controller 10 calculates the luminance distribution of the image data $I_1$ illustrated in FIG. 21. The image data $I_1$ illustrated in FIG. 21 includes a luminance value "α" and a luminance value "β" which are peaks, as illustrated in FIG. 22. The user operates the camera 13 and the mobile phone 100 by focusing on the indicator 41 of the body composition meter 40 being an object to be captured. Therefore, the image data $I_1$ includes a large portion of image as the indicator 41 of the body composition meter 40. Moreover, when the indicator 41 of the body composition meter 40 is formed of a liquid crystal panel that displays character information with a gray scale, luminance values of pixels forming the indicator 41 are basically the same values as each other. Thus, it is possible to determine that either one of the luminance value "α" and the luminance value "β" which are peaks is quite likely to be the indicator 41.

Figure 23:
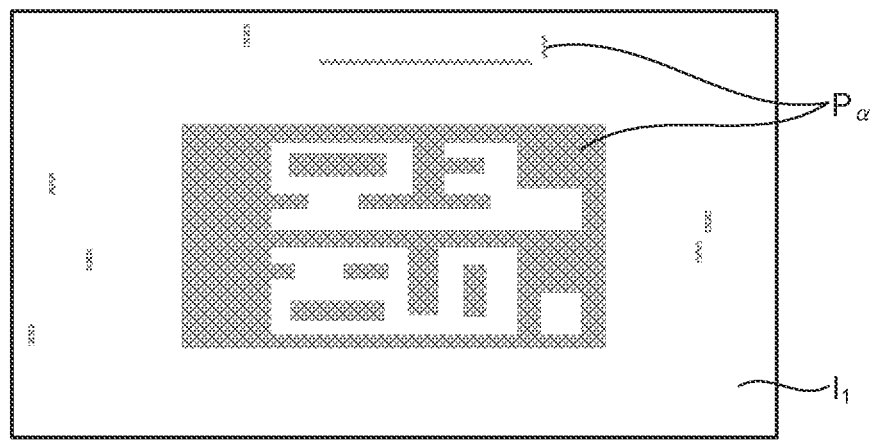
FIG. 23 is a diagram of one of examples of positions of pixels, in the image data, having a peak luminance value in the luminance distribution illustrated in FIG. 22.

FIG. 23 is a diagram of one of examples of positions of pixels, in the image data $I_1$, having a peak luminance value in the luminance distribution illustrated in FIG. 22. FIG. 23 depicts one of examples of positions of pixels $P_α$, in the image data $I_1$, having the luminance value "α" which is one of peaks in the luminance distribution illustrated in FIG. 22.

Figure 24:
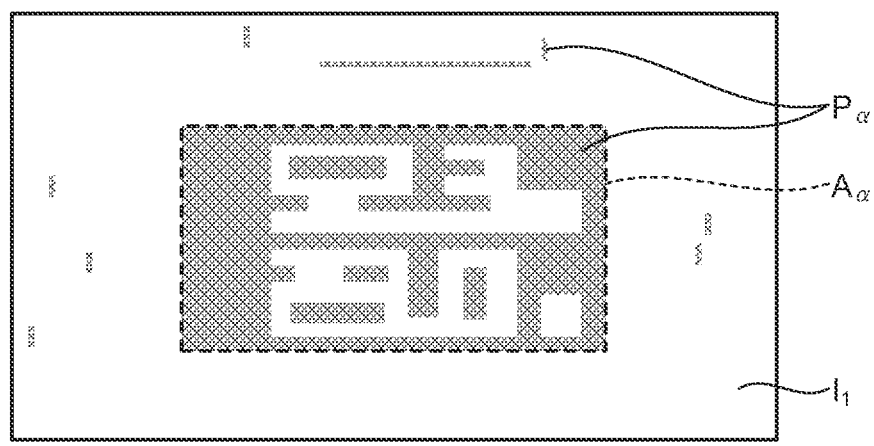
FIG. 24 is a diagram of one of examples of an area to be cut out as a candidate of an area in which an image of an indicator of a body composition meter appears.

FIG. 24 is a diagram of one of examples of an area to be cut out as a candidate of an area in which the image of the indicator 41 of the body composition meter 40 appears.

Because the user operates the camera 13 and the mobile phone 100 by focusing on the indicator 41 of the body composition meter 40 being an object to be captured, the image data $I_1$ can be predicted to include the large portion of image as the indicator 41 of the body composition meter 40. Therefore, the controller 10 refers to the positions (FIG. 23) of the pixels $P_α$, in the image data $I_1$, having the luminance value "α" which is one of peaks in the luminance distribution, and cuts out an area $A_α$ having a concentration of the pixels $P_α$ illustrated in FIG. 24 as a candidate of the area in which the image of the indicator 41 of the body composition meter 40 appears, from the image data $I_1$. For example, when the candidate of the area in which the image of the indicator 41 of the body composition meter 40 appears is to be cut out from the image data $I_1$, the controller 10 cuts out, for example, a minimum rectangle including an area having a concentration of the pixels $P_α$ which have one of the peak luminance values. The controller 10 can cut out an area in any one of various shapes such as a circle, an ellipse, and a triangle according to, for example, the shape of the area having a concentration of the pixels $P_α$.

The controller 10 performs the character recognition processing on the area $A_α$ cut out from the image data $I_1$ as a candidate of the area in which the image of the indicator 41 of the body composition meter 40 appears. When the character information can be recognized in the area $A_α$, the controller 10 specifies the area $A_α$ as an area in which the image of the indicator 41 of the body composition meter 40 appears.

When the area $A_α$ can be specified as an area in which the image of the indicator 41 of the body composition meter 40 appears, the controller 10 performs the photometric processing targeted at the area $A_α$. When the photometric processing targeted at the area $A_α$ is to be performed, the controller 10 may use any one of division photometry, centrally weighted photometry, and spot photometry. When the photometric processing is performed using the division photometry, the controller 10 divides the area $A_α$ into a plurality of areas, and calculates a control value used to determine an exposure amount from an average of light amounts in the divided areas. When the photometric processing is performed using the centrally weighted photometry, the controller 10 weights the light amount in a central area of the area $A_α$ to calculate a control value used to determine an exposure amount. When the photometric processing is performed using the spot photometry, the controller 10 calculates a control value used to determine an exposure amount based on a light amount in a slightly small portion of the area $A_α$.

Figure 25:
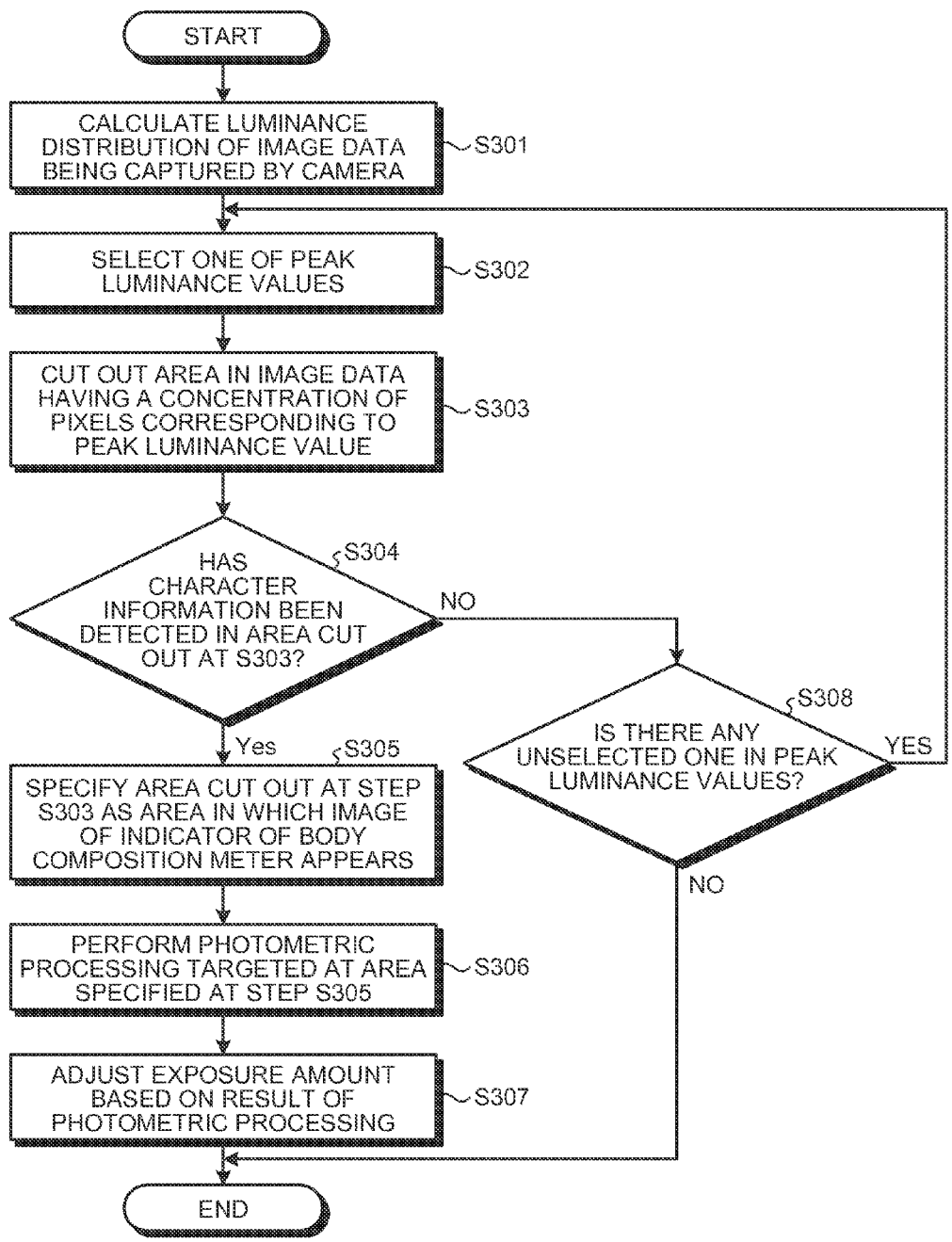
FIG. 25 is a diagram for explaining one of examples of a processing procedure in which the mobile phone specifies an area, in which an image of an indicator of a healthcare device appears, from the image data captured by the camera and performs photometric processing targeted at the specified area.

FIG. 25 is a diagram for explaining one of examples of a processing procedure in which the mobile phone 100 specifies an area, in which the image of the indicator of the healthcare device appears, from the image data captured by the camera 13 and performs photometric processing targeted at the specified area. The processing procedure illustrated in FIG. 25 is started by the controller 10 that activates the healthcare application 9D. The activation of the healthcare application 9D is performed in response to, for example, detection of a user operation similarly to the embodiment 1.

The controller 10 activates the camera 13 after the activation of the healthcare application 9D, and calculates a luminance distribution (see FIG. 22) of the image data $I_1$ (see FIG. 21, etc.) being captured by the camera 13 (Step S301). Subsequently, the controller 10 selects one (for example, α) of peak luminance values in the luminance distribution (Step S302).

Subsequently, the controller 10 cuts out an area (for example, $A_\alpha$, see FIG. 24), in the image data $I_1$, having a concentration of the pixels (for example, $P_\alpha$) which have the peak luminance value (Step S303).

The controller 10 then performs the character recognition processing on the area (for example, $A_\alpha$) cut out at Step S303 and determines whether the character information can be detected in the area (Step S304).

When it is determined that the character information can be detected in the area cut out at Step S303 (Yes at Step S304), the controller 10 specifies the area cut out at Step S303 as an area, in the image data $I_1$, in which the image of the indicator 41 of the body composition meter 40 appears (Step S305).

Subsequently, the controller 10 performs the photometric processing targeted at the area specified at Step S305 (Step S306). Then, the controller 10 adjusts the exposure amount of when the image data $I_1$ is captured and the image is acquired, based on the result of the photometric processing (Step S307), and ends the processing procedure illustrated in FIG. 25.

At Step S304, when it is determined that the character information cannot be detected in the area cut out at Step S303 (No at Step S304), the controller 10 determines whether there is any unselected one in the peak luminance values (Step S308). When it is determined that there is an unselected one (Yes at Step S308), the controller 10 returns to Step S302, selects one luminance value from unselected luminance values, and performs the above-described procedure. Meanwhile, when it is determined that there is no unselected one (No at Step S308), then the controller 10 ends the processing procedure illustrated in FIG. 25 without any change.

As explained above, in the embodiment 2, the mobile phone 100 executes the healthcare application 9D to thereby specify an area in the image data $I_1$ in which the image of the indicator of the healthcare device appears, based on the luminance distribution of the image data $I_1$ of the body composition meter 40 captured by the camera 13. Furthermore, the controller 10 executes the healthcare application 9D to thereby perform the photometric processing targeted at the specified area. Therefore, according to the embodiment 2, the measured value displayed in the indicator can be precisely read from the image obtained by capturing the indicator of the healthcare device.

In the embodiment 2, the mobile phone 100 cuts out an area in the image data $I_1$ corresponding to the peak luminance value in the luminance distribution as a candidate of an area in which the image of the indicator 41 appears. When the character information (for example, 7-segment) can be detected in the area cut out as a candidate, the mobile phone 100 specifies the area in the image data $I_1$ corresponding to the peak luminance value as an area in which the image of the indicator appears. The user operates the camera 13 and the mobile phone 100 by focusing on the indicator 41 of the body composition meter 40 being an object to be captured, and therefore the image data $I_1$ can be predicted to include a large portion of image as the indicator 41 of the body composition meter 40. Thus, a manner of performing the processing while determining the relevant area in the image data $I_1$ corresponding to the peak luminance value in the luminance distribution as an area in which the indicator 41 appears is effective. However, if any character information can be recognized in the relevant area, an area in which the image of the indicator 41 appears can be more surely specified.

In the embodiment 2, the area of the indicator 41 is specified based on the luminance distribution of the image data $I_1$ of the body composition meter 40. Therefore, for example, even when the position of the camera 13 does not face the body composition meter 40 directly, the measured value displayed in the indicator 41 can be precisely read. In other words, even when the image of the indicator 41 is captured at an angle, the photometric processing targeted at the indicator 41 is performed, and thus the measured value displayed in the indicator can be read without any influence such as the light reflected from the indicator 41 or the light reflected in the indicator 41.

The embodiment 2 has explained the examples of specifying the area in the image data $I_1$ in which the image of the indicator 41 of the body composition meter 40 appears based on the luminance distribution of the image data $I_1$ of the healthcare device 40 being captured by the camera 13. For example, the body composition meter 40 may be provided with a pattern design so as to specify an area in the image data $I_1$ in which the image of the indicator 41 of the body composition meter 40 appears.

Figure 26:
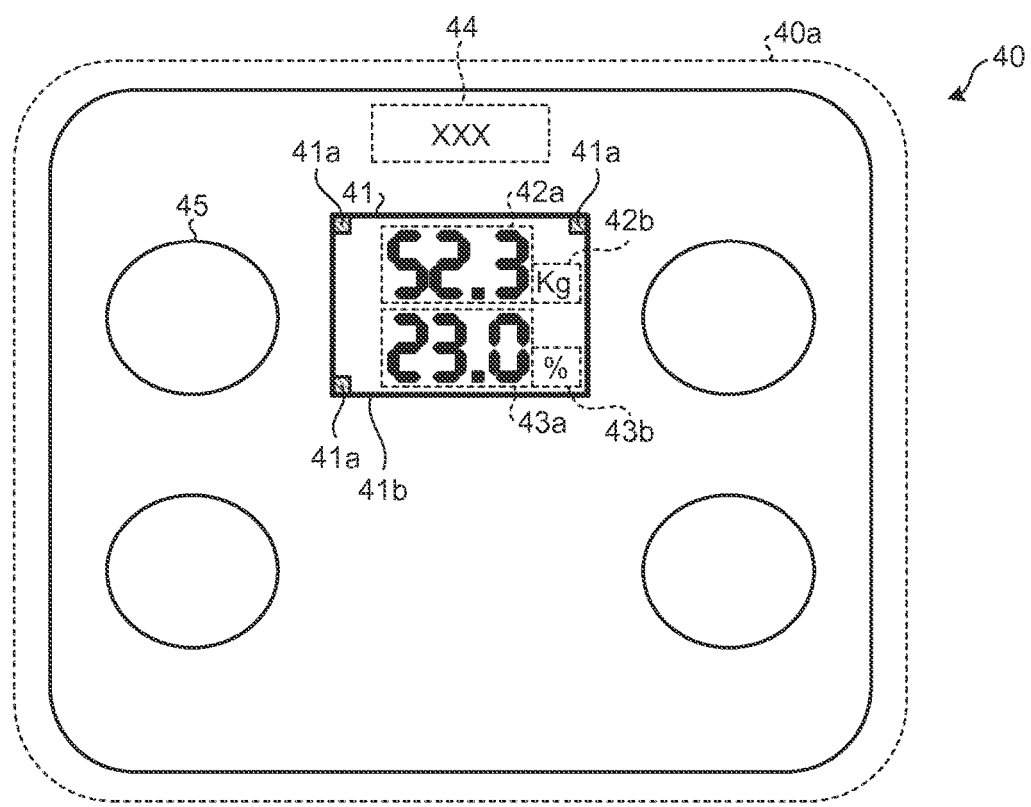
FIG. 26 is a diagram of one of examples of a pattern design for specifying an area in the image data in which an image of an indicator of a body composition meter appears.

FIG. 26 is a diagram of one of examples of a pattern design for specifying an area in the image data in which the image of the indicator 41 of the body composition meter 40 appears. As illustrated in FIG. 26, the pattern design is formed of three rectangles 41*a* arranged to be inscribed in three corners out of the four corners of the indicator 41 of the body composition meter 40, and a line 41*b* surrounding the indicator 41. When the image data for the body composition meter 40 is captured by the camera 13, the controller 10 recognizes the pattern design illustrated in FIG. 26, to thereby specify an area in the image data in which the image of the indicator 41 of the body composition meter 40 appears. The controller 10 may read the pattern design illustrated in FIG. 26 through pattern matching, or may read the pattern design illustrated in FIG. 26 by extracting edges from the image data.

An area of the indicator 41 may be specified not only by specifying the area of the indicator 41 in which the image of the indicator 41 of the body composition meter 40 appears by using the pattern design illustrated in FIG. 26 but also by detecting a display content of the indicator 41 and/or a change of the display content. For example, the controller 10 performs the character recognition processing on the image data for the body composition meter 40 being captured by the camera 13, and, when characters such as "in measuring" can be detected, specifies an area in which the image of the indicator 41 appears by using the position of the characters as a target. Alternatively, the controller 10 calculates an inter-frame difference of the image data for the body composition meter 40 being captured by the camera 13, and, when the change of the display content displayed in the indicator 41 during execution of measurement can be detected, specifies the area in which the image of the indicator 41 appears by using the changed portion as a target. The change of the display content includes a change of a numeral until a measured value of body weight is fixed, a change from a display of body weight to a display of body fat, and the like.

Alternatively, when the image data for the indicator 41 of the body composition meter 40 is captured by the camera 13, a guide frame or the like used to be fitted to the indicator 41 may be displayed on the display 2A. In this case, an area inside the guide frame, of the image data captured by the camera 13, is specified as an area in which the image of the indicator 41 appears.

The embodiment 2 has explained the examples of specifying the area of the indicator 41 of the body composition meter 40; however, the same way as that of the body composition meter 40 can be used to specify an indicator of healthcare devices other than the body composition meter 40, such as a thermometer, a blood pressure monitor for measuring blood pressure, a pulse meter for measuring pulses, a pedometer for counting steps, and an activity meter for measuring an amount of activity due to exercise including walking.

In the embodiment 2, when a color temperature of the indicator 41 of the body composition meter 40 or a type of the light source is previously found out, the mobile phone 100 can also adjust white balance according to the color temperature in the area of the indicator 41 or the type of the light source.

In the embodiment 2, the mobile phone 100 may change ISO sensitivity according to the result of photometric processing targeted at the area in which the image of the indicator 41 appears.

In the embodiment 2, it may be configured such that the mobile phone 100 narrows down an area, in which the indicator 41 in the image data for the body composition meter 40 being captured by the camera 13 appears, to some extent by using the used device information 9X, the determination information 9Y, and the like, and then specifies an area in which the indicator 41 appears, based on a luminance distribution of the narrowed down area.

The mobile phone 100 may perform the same processing as that of the embodiment 1 (Yes at Step S105 to Step S122) using the used device information 9X, the determination information 9, and the like after the measured value is acquired from the image captured by controlling the exposure amount based on the result of photometric processing targeted at the area of the indicator 41.

Embodiment 3

The mobile phone 100 may perform the control so that there is low possibility that the shadow of the mobile phone 100 or the mobile phone 100 itself unexpectedly appears in an image obtained by capturing the indicator of the healthcare device. How the shadow of the mobile phone 100 or the mobile phone 100 itself unexpectedly appears in the image will be explained below with reference to FIG. 27 to FIG. 30.

FIG. 27 is a diagram of one of examples of how the mobile phone 100 itself unexpectedly appears in an image. FIG. 28 is a diagram of one of examples of an image in which the mobile phone 100 itself unexpectedly appears. In the example illustrated in FIG. 27, the mobile phone 100 is held by the user substantially right above the body composition meter 40 in such a manner as to face the body composition meter 40 directly in order to capture an approximately rectangular indicator 41 (including a square) of the body composition meter 40 using the camera 13. In this case, when the surface of the indicator 41 is covered with a material that reflects light such as glass or transparent resin, the surface of the indicator 41 functions as a kind of mirror, and this may cause the mobile phone 100 itself to unexpectedly appear in an image captured by the camera 13.

For example, in a picture image P5 illustrated in FIG. 28, an image P5b of the mobile phone 100 unexpectedly appears inside an image P5a of the indicator 41. Such an unexpected appearance as above partially changes the luminance or the like of the image P5a, which may make it difficult to read the measured value included in the image P5a. Particularly, when a reflective display panel without a backlight is used for the indicator of a healthcare device, an amount of change in luminance of the indicator is originally small, and therefore the measured value may become difficult to be read due to a luminance difference produced by the unexpected appearance.

FIG. 29 is a diagram of one of examples of how the shadow of the mobile phone 100 unexpectedly appears in an image. FIG. 30 is a diagram of one of examples of an image in which the shadow of the mobile phone 100 unexpectedly appears. In the example illustrated in FIG. 29, the light source L1 is provided on the ceiling and the body composition meter 40 is placed on the floor. The mobile phone 100 is held by the user in between the light source L1 and the body composition meter 40 in order to capture the indicator 41 of the body composition meter 40 using the camera 13. In this case, a shadow of the mobile phone 100 occurs over the body composition meter 40 due to the light from the light source L1, and the shadow is likely to unexpectedly appear in the image captured by the camera 13. For the sake of simplicity, a user's body (especially, hand) by which the mobile phone 100 is held is not considered.

For example, in a picture image P6 illustrated in FIG. 30, an image P6b of the mobile phone 100 unexpectedly appears therein to overlap part of an image P6a of the indicator 41. The unexpected appearance of the shadow causes the luminance or the like of the image P6a to partially change, which may make it difficult to read the measured value included in the image P6a.

To prevent the unexpected appearance of the shadow of the mobile phone 100 or of the mobile phone 100 itself in the image, it is considered that the mobile phone 100 is inclined at a position away from right above the indicator 41 and the indicator 41 is captured, as illustrated in FIG. 31. FIG. 31 is a diagram of one of examples of a state in which the unexpected appearance does not occur. FIG. 32 is a diagram of one of examples of an image captured in the state illustrated in FIG. 31. In a picture image P7 illustrated in FIG. 32, neither the shadow of the mobile phone 100 nor the mobile phone 100 itself unexpectedly appears in an image P7a of the indicator 41. Because it is captured in the inclined state, the image P7a is distorted to an isosceles trapezoid in which its upper base is shorter than its bottom base, but by performing trapezoidal correction processing on the image P7a, the image P7a can be corrected to a rectangle suitable for reading the measured value.

Figure 33:
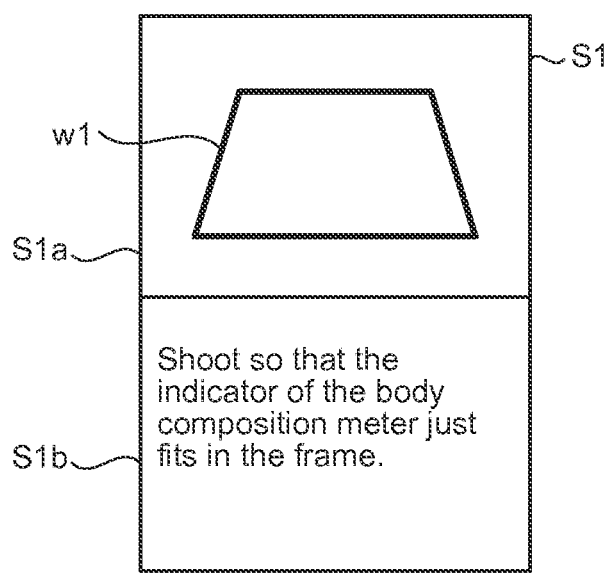
FIG. 33 is a diagram of one of examples of an image capture screen.

To cause the user to perform image capture in the state illustrated in FIG. 31, the control is simply performed so that the image of a substantially rectangular indicator of the healthcare device in an image captured by the camera 13 is formed to a trapezoid due to a difference in perspective between its upper side and lower side, as the picture image P7 illustrated in FIG. 32. Therefore, the mobile phone 100 can display an image capture screen S1 as illustrated in FIG. 33 on the display 2A when the indicator of the healthcare device is captured. FIG. 33 is a diagram of one of examples of the image capture screen S1.

The image capture screen S1 has an image display area S1a that occupies an upper half thereof and a message display area S1b that occupies a lower half thereof. The image display area S1a is an area in which an image captured by the camera 13 is continuously displayed. The image display area S1a includes a frame w1. The frame w1 has a shape of an isosceles trapezoid in which the upper base is shorter than the bottom base similarly to the image P7a of the indicator 41 in the picture image P7. The message display area S1b is an area in which a message for the user is displayed. In the example illustrated in FIG. 33, a message prompting the user to capture an image so that the indicator 41 of the body composition meter 40 just fits in the frame is displayed in the message display area S1b. The message display area S1b may further include a message prompting the user to incline the mobile phone 100.

By displaying the image capture screen S1 as described above on the display 2A, the frame w1 functions as a frame to which an outer shape of the image of the indicator of the healthcare device in the image captured by the camera 13 should be fitted. In other words, the user adjusts the position and inclination of the mobile phone 100 so that the outer shape of the image of the indicator of the healthcare device fits the frame w1 while viewing the image capture screen S1. Consequently, the capturing is performed in the state as illustrated in FIG. 31.

Figure 34:
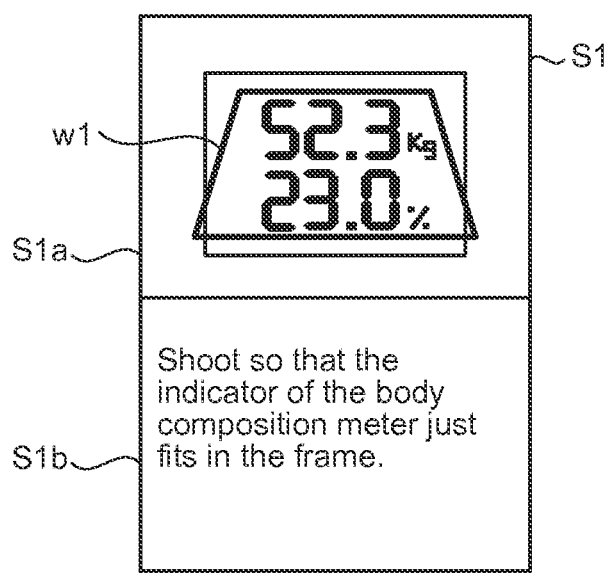
FIG. 34 is a diagram of one of examples of the image capture screen in a state where the mobile phone faces the healthcare device substantially directly.
Figure 35:
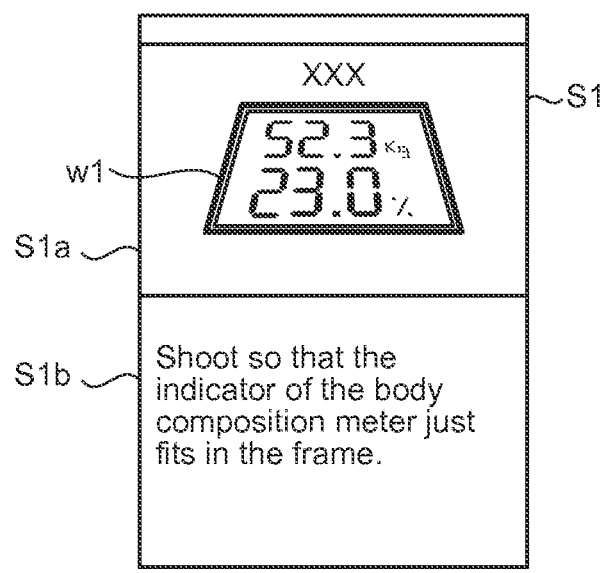
FIG. 35 is a diagram of one of examples of the image capture screen in the state illustrated in FIG. 31.

FIG. 34 is a diagram of one of examples of an image capture screen in a state of facing the healthcare device substantially directly. FIG. 35 is a diagram of one of examples of the image capture screen in the state illustrated in FIG. 31. For example, when the image capture is performed in the state in which the mobile phone 100 directly faces the body composition meter 40 substantially right above the body composition meter 40 as illustrated in FIG. 27 or FIG. 29, the image of the indicator 41 does not fit the frame w1 as illustrated in the example of FIG. 34. Therefore, the user can easily understand that the position and the inclination of the mobile phone 100 are not appropriate. The user then adjusts the position and the inclination of the mobile phone 100 so that the outer shape of the image of the indicator 41 fits the frame w1 as illustrated in the example of FIG. 35, thus achieving the state in which the picture image P7 illustrated in FIG. 32 is obtained, that is, achieving the state illustrated in FIG. 31.

Displaying the image capture screen S1 including the trapezoidal frame w1 in the above manner allows the user to perform capturing in a suitable condition without giving a complicated instruction to the user. Moreover, by using this technique, it can be expected that the shape of the image of the indicator 41 included in the captured image becomes substantially constant. Therefore, a correction coefficient of trapezoidal correction for correcting the shape of the image of the indicator 41 to a rectangle in order to read the measured value included in the image can be determined in advance, thus reducing the load of image processing.

Figure 36:
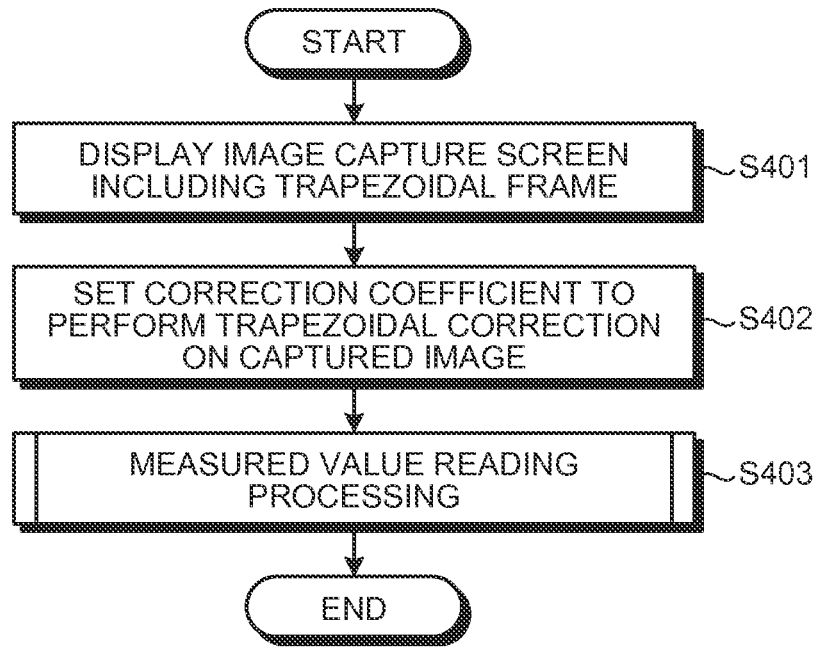
FIG. 36 is a flowchart of one of examples of control for reducing a possibility for occurrence of the unexpected appearance.

A control for reducing a possibility that the unexpected appearance of the shadow of the mobile phone 100 or the mobile phone 100 itself occurs will be explained with reference to FIG. 36. FIG. 36 is a flowchart of one of examples of control for reducing a possibility for occurrence of the unexpected appearance. The control illustrated in FIG. 36 is implemented by the controller 10 executing the healthcare application 9D.

As illustrated in FIG. 36, at Step S401, the controller 10 displays the image capture screen S1 including the trapezoidal frame w1 on the display 2A. Then, at Step S402, the controller 10 sets a correction coefficient to perform trapezoidal correction on the captured image. The correction coefficient set herein is, for example, a coefficient for correcting the shape of the frame w1 to a rectangle. Thereafter, at Step S403, the controller 10 performs the processing illustrated in FIG. 9. In the processing, the controller 10 performs trapezoidal correction on the image captured by the camera 13 using the correction coefficient set at Step S402 before reading the numeral, symbol, and the like included in the image captured by the camera 13.

The controller 10 may dynamically change the shape of the frame w1 to be displayed on the display 2A during execution of the processing illustrated in FIG. 9. For example, when the distortion of the image of the indicator 41 in the image is too large to read the numerals or the like, the controller 10 may perform at least one of the control for elongating the upper base of the frame w1 and the control for widening a distance between the upper base and the lower base of the frame w1. By changing the shape of the frame w1 in this manner, it is possible to lead the user to change the position and the inclination of the mobile phone 100 in a direction in which the distortion of the frame w1 is reduced, in other words, to change them so that the mobile phone 100 and the body composition meter 40 face each other more directly. For example, when the numeral and the like included in the image of the indicator 41 cannot be read entirely, it is possible to determine that the distortion of the image is too large.

Alternatively, when the numeral and the like are difficult to be read due to the unexpected appearance of the shadow of the mobile phone 100 or of the mobile phone 100 itself in the image, the controller 10 may perform at least one of the control for shortening the upper base of the frame w1 and the control for narrowing the distance between the upper base and the lower base of the frame w1. By changing the shape of the frame w1 in this manner, it is possible to lead the user to change the position and the inclination of the mobile phone 100 in a direction in which the unexpected appearance is difficult to occur, in other words, to change them so that the mobile phone 100 and the body composition meter 40 face each other less directly. For example, when the numeral and the like included in the image of the indicator 41 cannot be read partially, it is possible to determine that the unexpected appearance occurs.

When the shape of the frame w1 is dynamically changed in this manner, the controller 10 changes the correction coefficient set at Step S402 in accordance with the shape of the frame w1 after the change.

Figure 37:
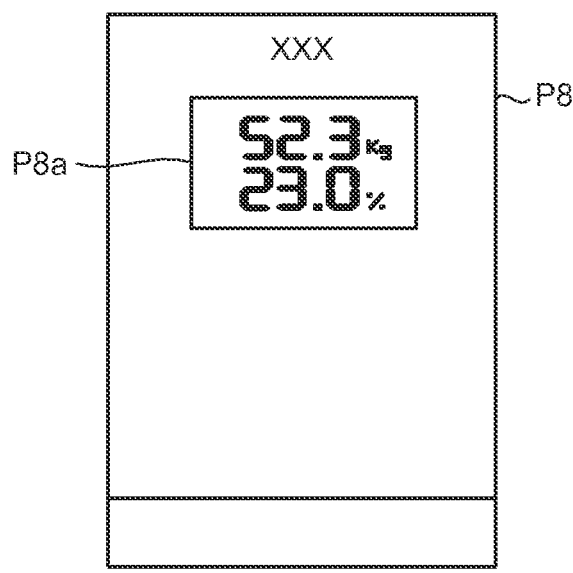
FIG. 37 is a diagram of one of examples in which trapezoidal correction is performed on the captured image in the state illustrated in FIG. 31.

In the above explanation, the example of displaying the trapezoidal frame w1 is described as one of examples of display control for reducing the possibility that the shadow of the mobile phone 100 or the mobile phone 100 itself unexpectedly appears in the image; however, the display control is not limited thereto. For example, the controller 10 may display the image, as the image capture screen, obtained by performing the trapezoidal correction thereon using the correction coefficient to be set at Step S402 illustrated in FIG. 36 on the display 2A instead of displaying the trapezoidal frame w1 thereon. With this control, for example, the picture image P7 (see FIG. 32) captured in the state illustrated in FIG. 31 is displayed as an image with no distortion like a picture image P8 illustrated in FIG. 37. FIG. 37 is a diagram of one of examples in which trapezoidal correction is performed on the image captured in the state illustrated in FIG. 31. An image P8a of the indicator 41 illustrated in FIG. 37 is an image in which the shape of the image P7a distorted to the isosceles trapezoid with the upper base shorter than the lower base is corrected to the rectangle through the trapezoidal correction.

Figure 38:
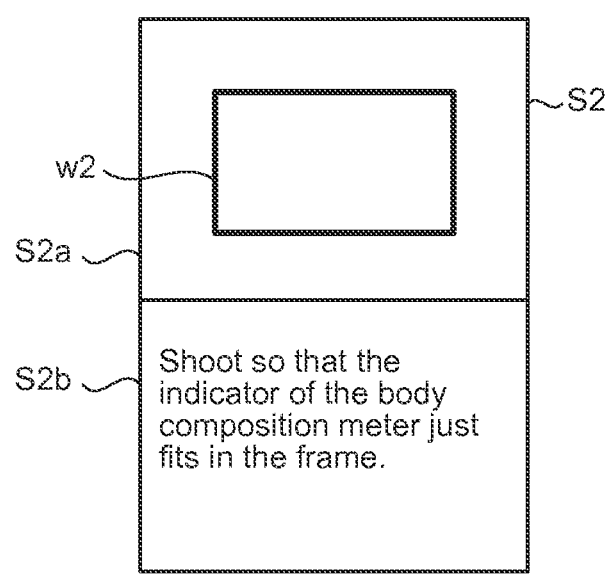
FIG. 38 is a diagram of another example of the image capture screen.

In this case, the mobile phone 100 displays an image capture screen S2 as illustrated in FIG. 38 on the display 2A when the indicator of the healthcare device is captured. FIG. 38 is a diagram of another example of the image capture screen. The image capture screen S2 has an image display area S2a that occupies an upper half thereof and a message display area S2b that occupies a lower half thereof. The image display area S2a is an area in which an image captured by the camera 13 is continuously displayed. The image display area S2a includes a frame w2. The frame w2 has a rectangular shape. The image display area S2a does not have to include the frame w2. The message display area S2*b* is an area in which a message for the user is displayed. In the example illustrated in FIG. 38, a message prompting the user to capture an image so that the indicator 41 of the body composition meter 40 just fits in the frame is displayed in the message display area S2*b*.

Figure 39:
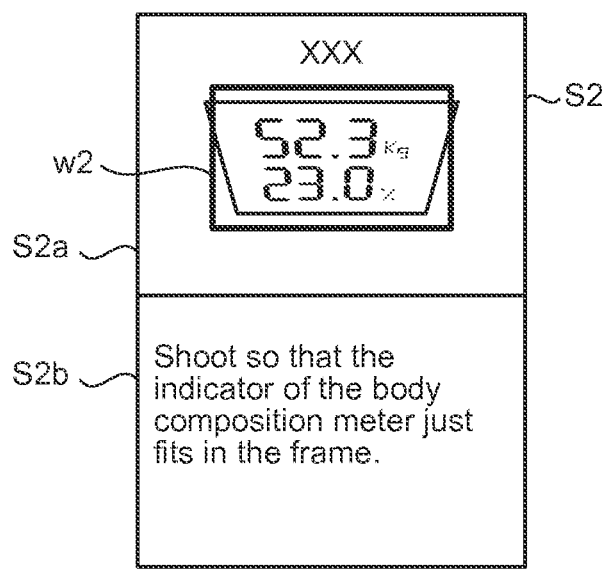
FIG. 39 is a diagram of one of examples of the image capture screen in a state where the mobile phone faces the healthcare device substantially directly.
Figure 40:
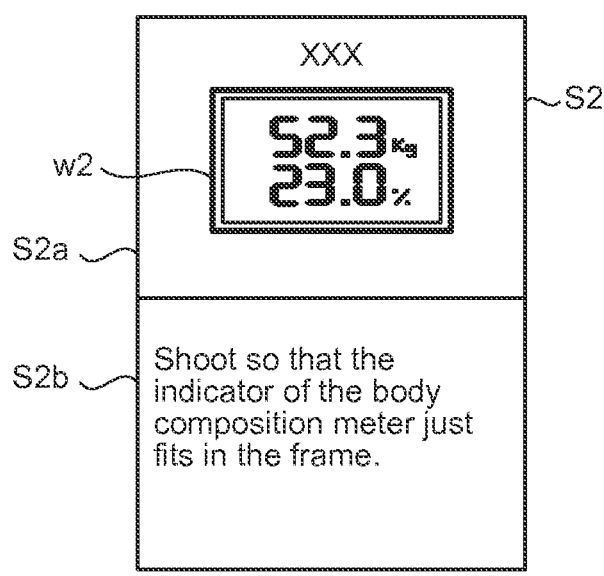
FIG. 40 is a diagram of one of examples of the image capture screen in the state illustrated in FIG. 31.

FIG. 39 is a diagram of one of examples of an image capture screen in a state of facing the healthcare device substantially directly. FIG. 40 is a diagram of one of examples of the image capture screen in the state illustrated in FIG. 31. For example, when the capturing is performed in the state in which the mobile phone 100 directly faces the body composition meter 40 substantially right above the body composition meter 40 as illustrated in FIG. 27 or FIG. 29, the image of the indicator 41 is distorted to a trapezoidal shape, as illustrated in the example of FIG. 39, in which the upper side is longer than the lower side because the trapezoidal correction is performed thereon, and furthermore the image does not fit the frame w2. Therefore, the user can easily understand that the position and the inclination of the mobile phone 100 are not appropriate. The user then adjusts the position and the inclination of the mobile phone 100 so that the outer shape of the image of the indicator 41 fits to the frame w2 while eliminating the distortion of the image as illustrated in the example of FIG. 40, thus achieving the state in which the picture image P8 illustrated in FIG. 37 is obtained, that is, achieving the state illustrated in FIG. 31.

Displaying the image after the trapezoidal correction in the above manner also allows the user to perform capturing in the suitable condition without giving a complicated instruction to the user. Moreover, by using this technique, the user adjusts the position and inclination of the mobile phone 100 so as to reduce the distortion in the displayed image, that is, in the image from which the measured value is read, and this enables accurate reading of the measured value using the image with less distortion.

In other words, the present embodiment is implemented by using the psychology of the user such as "I want the mobile phone to face the body composition meter 40 directly". In other words, it is implemented by using the psychology of the user such that when the image of the indicator 41 is distorted as illustrated in FIG. 39, this causes the user to make a mistake that the mobile phone 100 does not face the body composition meter 40 directly and he/she tries inclining the mobile phone 100 as illustrated in FIG. 31.

The embodiment represents the examples of displaying the trapezoidal frame w1 and the image of the indicator 41 illustrated in FIG. 39 in a trapezoid in which the upper side and the lower side are parallel to each other. However, the embodiment is not limited thereto if it is possible to make the user be aware that the mobile phone 100 and the body composition meter 40 should not face each other directly.

The embodiments have explained the mobile phone as one of examples of the electronic device; however, the electronic device according to the appended claims is not limited to the mobile phone. The electronic device according to the appended claims may be any mobile electronic device other than the mobile phone. Examples of the mobile electronic device includes, but are not limited to, a tablet, a mobile personal computer, a digital camera, a media player, an electronic book reader, a navigator, and a gaming device. The electronic device according to the appended claims may be any electronic device other than the mobile electronic device.

Although the art of appended claims has been described with respect to specific embodiments for a complete and clear disclosure, the appended claims are not to be thus limited but are to be construed as embodying all modifications and alternative constructions that may occur to one skilled in the art which fairly fall within the basic teaching herein set forth.

The invention claimed is:

1. An electronic device, comprising:
    a camera; and
    a controller configured
        to determine whether a measured numerical value of a healthcare device is included in an image captured by the camera,
        to cause information related to the measured numerical value to be transmitted to an information providing device when the measured numerical value is included in the image, and
        to perform control so as to match (i) an orientation of the image captured by the camera to (ii) an orientation of an indicator in said image, said indicator indicating the measured numerical value of the healthcare device.

2. The electronic device according to claim 1, wherein
    the controller is configured to perform the control when it is determined that the measured numerical value of the healthcare device is included in a video being captured by the camera.

3. The electronic device according to claim 1, further comprising a display configured to display a video being captured by the camera, wherein,
    when an orientation of the video being captured by the camera does not match the orientation of the indicator,
        the controller is configured to change the orientation of the video.

4. The electronic device according to claim 1, further comprising a display configured to display a message prompting to change an orientation of the electronic device when an orientation of a video being captured by the camera does not match the orientation of the indicator.

5. The electronic device according to claim 1, further comprising a display configured to display a video being captured by the camera, wherein,
    when the orientation of the video being captured does not match the orientation of the indicator,
        the controller is configured to cause the display not to display the video being captured.

6. The electronic device according to claim 1, further comprising a display configured to,
    when the camera faces the indicator of the healthcare device directly,
        display the indicator being captured by the camera in such a manner as to be formed to a trapezoid.

7. The electronic device according to claim 1, further comprising a display configured to display a video being captured by the camera, wherein
    the controller is configured to control displaying by the display so that an image of the indicator indicating the measured numerical value of the healthcare device in the video being captured by the camera is formed to a trapezoid.

8. The electronic device according to claim 7, wherein
    the controller is configured to cause the display to display a trapezoidal frame fit to an outer shape of the image of the indicator in the video being captured by the camera.

9. The electronic device according to claim 7, wherein the controller is configured to
- read the measured numerical value indicated in the indicator from an image in which a shape of the image of the indicator captured by the camera is corrected, and
- display the corrected image on the display.

10. An information providing system, comprising:
an electronic device; and
an information providing device, wherein
the electronic device includes:
- a camera; and
- a first controller configured
  - to determine whether a measured numerical value of a healthcare device is included in an image captured by the camera,
  - to cause information related to the measured numerical value to be transmitted to an information providing device when the measured numerical value is included in the image, and
  - to perform control so as to match (i) an orientation of the image captured by the camera to (ii) an orientation of an indicator in said image, said indicator indicating the measured numerical value of the healthcare device; and the information providing device includes:
- a storage configured to store the information related to the measured numerical value; and
- a second controller configured to perform analysis based on the information related to the measured numerical value.

11. The information providing system according to claim 10, wherein
the electronic device further includes a display configured to display a video being captured by the camera, and
the first controller is configured to control displaying by the display so that an image of the indicator indicating the measured numerical value of the healthcare device in the video being captured by the camera is formed to a trapezoid.

12. The information providing system according to claim 10, wherein
the electronic device further includes a display configured to,
- when the camera faces the indicator of the healthcare device directly,
  - display the indicator being captured by the camera in such a manner as to be formed to a trapezoid.

13. A control method of an electronic device with a camera, the control method comprising:
- determining whether a measured numerical value of a healthcare device is included in an image captured by the camera;
- performing analysis for providing information based on information related to the measured numerical value; and
- performing control so as to match (i) an orientation of the image captured by the camera to (ii) an orientation of an indicator in said image, said indicator indicating the measured numerical value of the healthcare device.

14. The control method according to claim 13, wherein
the performing control is executed when it is determined that the measured numerical value of the healthcare device is included in a video being captured by the camera.

15. The control method according to claim 13, further comprising:
- displaying a video being captured by the camera on a display provided in the electronic device; and
- controlling displaying by the display so that an image of the indicator indicating the measured numerical value of the healthcare device in the video being captured by the camera is formed to a trapezoid.

16. The control method according to claim 13, further comprising:
- displaying, when the electronic device faces the indicator of the healthcare device directly, the indicator being captured by the camera in such a manner as to be formed to a trapezoid on a display provided in the electronic device.

17. A non-transitory storage medium that stores a control program that causes, when executed by an electronic device with a camera, the electronic device to execute:
- determining whether a measured numerical value of a healthcare device is included in an image captured by the camera;
- performing analysis for providing information based on information related to the measured numerical value; and
- performing control so as to match (i) an orientation of the image captured by the camera to (ii) an orientation of an indicator in said image, said indicator indicating the measured numerical value of the healthcare device.

18. An electronic device, comprising:
- a camera configured to capture an image of a display of a healthcare device;
- a display configured to display the image captured by the camera; and
- a controller configured to
  - cause the display to display a trapezoidal frame a shape of which is to be fitted to a shape of the display of the healthcare device in the image captured by the camera,
  - read a measured numerical value presented in the image captured by the camera within the trapezoidal frame, and
  - change the shape of the trapezoidal frame when the controller cannot read the measured numerical value presented in the image within the trapezoidal frame.

* * * * *